(12) United States Patent
Edgar et al.

(10) Patent No.: US 11,475,358 B2
(45) Date of Patent: Oct. 18, 2022

(54) ANNOTATION PIPELINE FOR MACHINE LEARNING ALGORITHM TRAINING AND OPTIMIZATION

(71) Applicant: GE Precision Healthcare LLC, Milwaukee, WI (US)

(72) Inventors: Marc T. Edgar, Glenmont, NY (US); Travis R. Frosch, Orlando, FL (US); Gopal B. Avinash, San Ramon, CA (US); Garry M. Whitley, Clinton, TN (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 662 days.

(21) Appl. No.: 16/527,965

(22) Filed: Jul. 31, 2019

(65) Prior Publication Data
US 2021/0034920 A1 Feb. 4, 2021

(51) Int. Cl.
*G06N 20/00* (2019.01)
*G06N 5/04* (2006.01)
(Continued)

(52) U.S. Cl.
CPC .......... *G06N 20/00* (2019.01); *G06F 40/169* (2020.01); *G06K 9/6228* (2013.01);
(Continued)

(58) Field of Classification Search
CPC .......... G06N 5/04; G06N 5/048; G06N 20/00; G16H 50/20; G06F 40/169; G06V 10/771;
(Continued)

(56) References Cited

U.S. PATENT DOCUMENTS 10,140,421 B1  11/2018  Bernard et al.
2017/0185670 A1  6/2017  Dua et al.
(Continued)

FOREIGN PATENT DOCUMENTS

WO  2018104342 A1  6/2018

OTHER PUBLICATIONS

International Application No. PCT/US2020/042845 filed Jul. 21, 2020—International Search Report and Written Opinion dated Oct. 5, 2020; 16 pages.
(Continued)

*Primary Examiner* — Daniel G Mariam
(74) *Attorney, Agent, or Firm* — Amin, Turocy & Watson, LLP

(57) ABSTRACT

Techniques are provided for enhancing the efficiency and accuracy of annotating data samples for supervised machine learning algorithms using an advanced annotation pipeline. According to an embodiment, a method can comprise collecting, by a system comprising a processor, unannotated data samples for input to a machine learning model and storing the unannotated data samples in an annotation queue. The method further comprises determining, by the system, annotation priority levels for respective unannotated data samples of the unannotated data samples, selecting, by the system from amongst different annotation techniques, one or more of the different annotation techniques for annotating the respective unannotated data samples based the annotation priority levels associated with the respective unannotated data samples.

32 Claims, 15 Drawing Sheets

(51) Int. Cl.
*G16H 50/20* (2018.01)
*G06F 40/169* (2020.01)
*G06K 9/62* (2022.01)

(52) U.S. Cl.
CPC ......... *G06K 9/6257* (2013.01); *G06K 9/6259* (2013.01); *G06K 9/6264* (2013.01); *G06N 5/04* (2013.01); *G06N 5/048* (2013.01); *G16H 50/20* (2018.01)

(58) Field of Classification Search
CPC ........... G06V 10/7747; G06V 10/7753; G06V 10/7788
See application file for complete search history.

(56) References Cited

U.S. PATENT DOCUMENTS

| | | | |
|---|---|---|---|
| 2018/0068221 | A1 | 3/2018 | Brennan et al. |
| 2018/0068222 | A1 | 3/2018 | Brennan et al. |
| 2019/0205606 | A1 | 7/2019 | Zhou et al. |
| 2019/0347524 | A1 | 11/2019 | Znamenskiy et al. |
| 2020/0202171 | A1 | 6/2020 | Hughes et al. |
| 2020/0380311 | A1 | 12/2020 | Lourentzou et al. |
| 2021/0042916 | A1* | 2/2021 | Zhang .................... A61B 6/50 |

OTHER PUBLICATIONS

Li et al: "Sample awareness-based personalized facial expression recognition," Applied Intelligence, Kluwer Academic Publishers, Dordrecht, NL, vol. 49, No. 8, Feb. 13, 2019 (Feb. 13, 2019), pp. 2956-2969, [retrieved on Feb. 13, 2019], 14 pages.

Non-Final Office Action received for U.S. Appl. No. 16/528,121 dated Sep. 3, 2021, 71 pages.

Zhang et al., "Radiological Images and Machine Learning: Trends, Perspectives, and Prospects", Computers in Biology and Medicine, 2019, vol. 108, pp. 354-370.

Li et al., "Confidence-based Active Learning", IEEE Transactions on Pattern Analysis and Machine Intelligence, 2006, vol. 28, No. 8, pp. 1251-1261.

Final Office Action received for U.S. Appl. No. 16/528,121 dated Mar. 4, 2022, 42 pages.

* cited by examiner

ANNOTATION PIPELINE FOR MACHINE LEARNING ALGORITHM TRAINING AND OPTIMIZATION

TECHNICAL FIELD

This application generally relates to supervised machine learning and more particularly to an advanced annotation pipeline for machine learning algorithm training and optimization.

SUMMARY

The following presents a summary to provide a basic understanding of one or more embodiments of the invention. This summary is not intended to identify key or critical elements or to delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products are described that provide an annotation pipeline for machine learning algorithm training and optimization.

According to an embodiment, a system can comprise a memory that stores computer executable components and a processor that executes the computer executable components stored in the memory. The computer executable components can comprise a collection component that collects unannotated data samples for input to a machine learning model and stores the unannotated data samples in an annotation queue. The computer executable components can further comprise a priority evaluation component that determines annotation priority levels for respective unannotated data samples of the unannotated data samples, and an annotation management component that selects, from amongst different annotation techniques, one or more of the different annotation techniques for annotating the respective unannotated data samples based the annotation priority levels associated with the respective unannotated data samples.

For example, in one or more implementations, the different annotation techniques are selected from a group consisting of, a manual annotation technique, a supervised learning annotation technique, and a metadata extraction annotation technique. In various exemplary embodiments, the data samples comprise medical images and the machine learning model can be configured to generate medical inferences regarding a medical condition or disease based on the medical images.

In some implementations, the annotation management component can select a subset of the unannotated data samples for annotating based on the annotation priority levels associated with the respective unannotated data samples. For example, the annotation management component can select a subset of the unannotated data samples that are determined to be associated with an annotation priority level above a certain threshold (e.g., select the higher priority samples for annotating before the lower priority samples). In another implementation, the different annotation techniques can comprise a first annotation technique and a second annotation technique, and the annotation management component can select the first annotation technique for a first subset of the unannotated data samples based on association of the first subset with a first annotation priority level of the annotation priority levels, and selects the second annotation technique for a second subset of the unannotated data samples based on association of the second subset with a second annotation priority level of the annotation priority levels. For example, in one implementation, the first annotation technique can comprise a manual annotation technique for application to unannotated data samples associated with a high priority level, and the second annotation technique can comprise an automated annotation technique for application to unannotated data samples associated with a low priority level.

In one or more embodiments, the priority evaluation component can determine the annotation priority levels based on estimated confidence in the accuracy of inferences that would be generated based on application of the machine learning model to respective unannotated data samples of the unannotated data samples. In other embodiments, the priority evaluation component can determine the annotation priority levels based on a quantity of annotated training data samples used to train the machine learning model that correspond to the respective unannotated data samples. In other implementations, the priority evaluation component can determine the annotation priority levels based on attributes associated with the respective unannotated data samples and correlations between the attributes and accuracy of performance of the machine learning model on previous data samples comprising the attributes. With these implementations, the computer executable components can further comprise an active learning component that employ one or more machine learning techniques to learn the correlations. For example, the active learning component can learn one or more attributes of the attributes that are associated with a degree of accuracy of the performance of the machine learning model that is below a threshold degree of accuracy, and the priority evaluation component can assign a high annotation priority level to a subset of the unannotated data samples based on the subset comprising the one or more attributes. Likewise, the active learning component can learn one or more attributes of the attributes that are associated with a degree of accuracy of the performance of the machine learning model that is above a threshold degree of accuracy, and the priority evaluation component can assign a low annotation priority level to a subset of the unannotated data samples based on the subset comprising the one or more attributes.

In various implementations, the computer executable components further comprise an annotation component that facilitates applying the one or more different annotation techniques to the unannotated data samples to generate annotations for the respective unannotated data samples, thereby transforming the unannotated data samples into annotated data samples. With these implementations, the computer executable components can further comprise an active learning component that evaluates the annotations and determines levels of confidence in the annotations. For example, in some embodiments, the active learning component can apply the machine learning model to the respective unannotated data samples to determine the levels of confidence. In one or more implementations, the active learning component can further identify a subset of the annotated data samples for reannotating based on the annotations associated therewith having a level of confidence that is below a level of confidence and send the subset back to the annotation queue. The computer executable components can further comprise a feedback component that generates feedback information regarding the subset and facilitates rendering the feedback information at a device associated with an entity responsible for reviewing the subset. The active learning component can also identify a subset of the annotated data samples associated with annotations having a level of confidence that is above a threshold level of confidence and adds the subset to a set of annotated training data samples for training or updating the machine learning model. The computer executable components further comprise a model development module that employs the set of annotated training data samples to train or update the machine learning model.

In some embodiments, elements described in connection with the system can be embodied in different forms such as a computer-implemented method, a computer program product, or another form.

DETAILED DESCRIPTION

Figure 1:
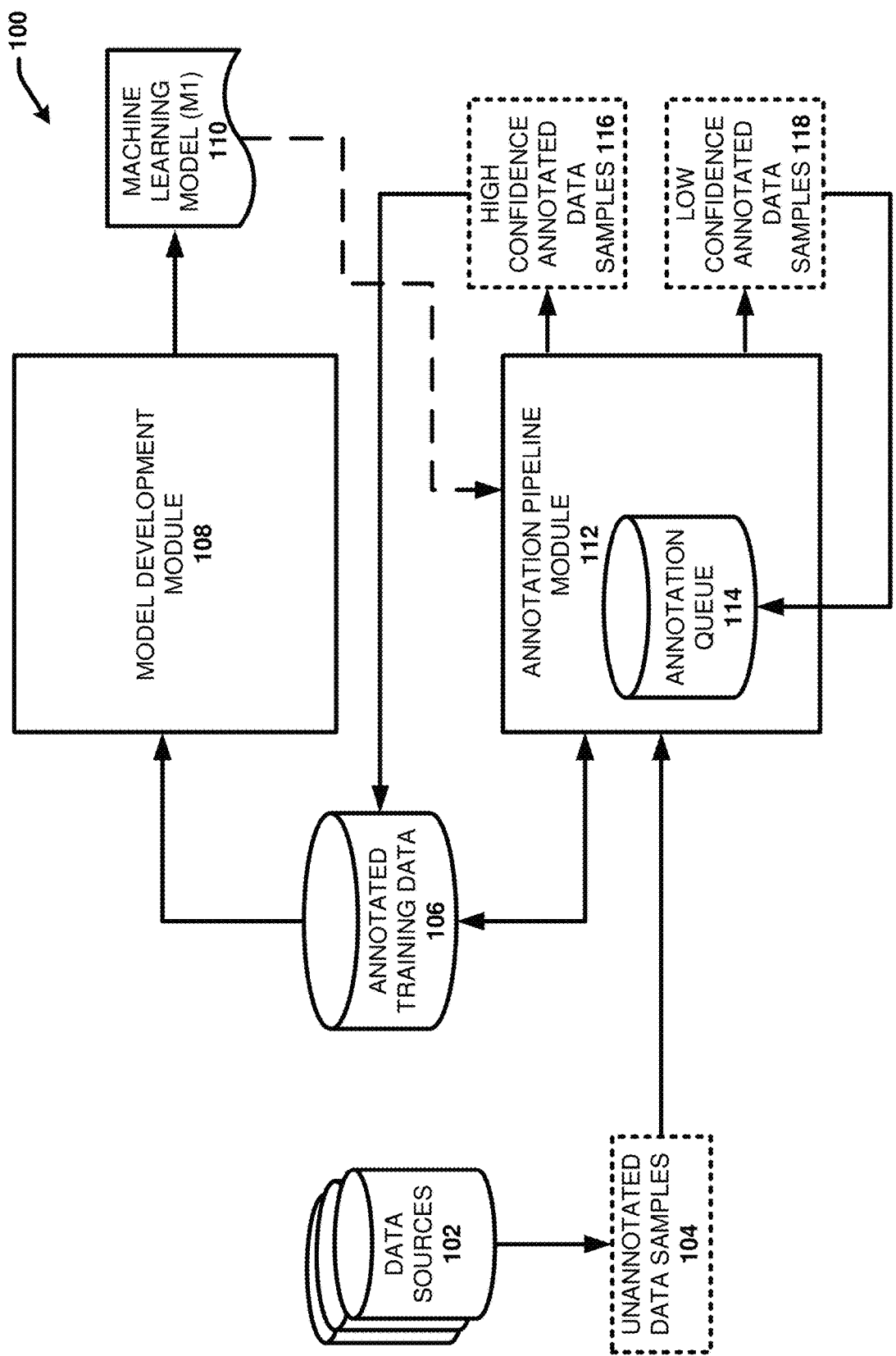
FIG. 1 illustrates a block diagram of an example, non-limiting system that facilitates enhancing the efficiency and accuracy of annotating data samples for supervised machine learning algorithms in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

Artificial intelligence (AI) and machine learning (ML) is a rapidly progressing technical field impacting a wide range of industries. Advancements in machine learning technologies, such as deep neural networks (DNN)s, have recently shown impressive performance, sometimes exceeding humans, in various AI domains, including computer vision, speech, natural language processing (NPL), bioinformatics, drug design, medical image analysis, and more. For example, AI can be used in medical imaging to automatically characterize features in images to make radiologists more efficient, minimize errors, and help them make their reports more quantitative and useful for the patients they serve. However, the development of AI models capable of generating inferences with the level of accuracy and consistency required for clinical applications is limited by the fact that these types of models must be trained and validated using mass amounts of accurately annotated training data, which is often not available or expensive and difficult to obtain.

In particular, machine learning algorithms can be categorized into two broad classes, supervised and unsupervised. Unsupervised learning methods have been investigated and researched the past few decades and, while encouraging, the maturity and robustness of these methods do not warrant themselves yet to the rigor needed for many advanced applications, such as medical/clinical applications. Supervised learning techniques however have been showing great promise due to computational and theoretical breakthroughs in the recent years. In a supervised paradigm, the learning system is first given examples of data by which human teachers or annotators apply classification labels to a corpus of data. The class labels are then used by the learning algorithm to adapt and change its' internal, mathematical representation (such as the behavior of artificial neural networks) of the data and mapping to some predication of classification. The training consists of iterative methods using numerical, optimization techniques that reduce the error between the desired class label and the algorithm's prediction. The newly trained model is then given new, unlabeled data as an input and, if trained well, can classify or otherwise provide an assessment of the new data.

Because the supervised training paradigm is dependent upon rich and varied data, it is imperative that training data be accurate and represent all or most of the variants the algorithm could 'see' when new data is presented to it. For example, consider development of a diagnostic model configured to evaluate chest x-rays to classify them as normal versus abnormal. There could be hundreds of different variables that would make an x-ray abnormal. Thus, to train the diagnostic model, a corpus of training data would be needed that shows all the possible representations of all those different variables compared to representations that would be classified as normal. That could add up to hundreds of thousands or even millions of images, all of which would need to be labeled and annotated in a consistent manner.

Currently techniques for generating annotated training data for machine learning in healthcare informatics are inefficient, burdensome and prone to error. For example, to create the training data needed to generate accurate medical imaging diagnostic models, human experts must label the images and define which elements are normal and which should be flagged. In this regard, the mapping of image features based on the physics of the acquisition to underlying physiology, function and anatomy is the core of the science and art of diagnostic radiology, cardiology and pathology. Thus, to create sufficient training data for medical imaging-based diagnostics, human annotators must evaluate image data sets to detect and interpret a large variety of pathophysiology and artifacts in medical imagery and further accurately and consistently label the artifacts. The collection of data sets in a retrospective training setting by which a human expert sorts through and highlights and classifies findings on pre-selected exams can be extremely tedious, expensive and time-consuming. This process can become exponentially inefficient and infeasible when applied to generate tailored algorithms for many different types of medical conditions, different types of medical images, different patient groups (e.g., grouped by age, gender, location or another distinguishing criteria) and the like. In addition, because it involves fallible and opinionated human experts defining what the algorithm will be looking for, it's also an opportunity for unconscious bias to creep in. Annotation is thus a considerable part of the challenge of creating machine learning algorithms in the healthcare field.

The disclosed subject matter provides systems, computer-implemented methods, apparatus and/or computer program products that facilitate enhancing the efficiency and accuracy of annotating data samples for training machine learning algorithms using an advanced annotation pipeline. For example, in various implementation, the machine learning algorithms can include a DNN model configured to evaluate medical images and generate inferences regarding a medical condition or disease reflected in the medical images. For instance, the DNN model can be configured to diagnose presence or absence of a particular medical condition based on analysis of the medical image data, classify a severity level of a disease state based on analysis of the medical image data, or the like. Regardless of the specific classification function of the machine learning model, the machine learning model can be developed and trained in accordance with a supervised learning paradigm based on annotated training data samples. The advanced annotation pipeline provides techniques for efficiently generating these annotated training data samples using one or more annotation techniques. In some embodiments, an initial set of manually annotated training images can be provided to initiate training and development of the machine learning model. With these embodiments, after initial training and development of the machine learning model, the advanced annotation pipeline can facilitate generating and adding additional annotated training data samples to the initial training data set in accordance with the techniques described herein. The additional annotated training data samples can be used to further train and refine the machine learning model over time.

In this regard, in one or more embodiments, the advanced annotation pipeline can include an annotation queue that collects unannotated data samples. The advanced annotation pipeline can further include an annotation component that facilitates annotating the unannotated data samples using one or more annotation techniques. In various embodiments, the one or more annotations techniques can include at least an automated annotation technique and a manual (e.g., human based) annotation technique. In various embodiments, the automated annotation technique can include a semi-supervised machine learning technique wherein the machine learning model itself is applied to the unannotated data sample to generate an inference result. In some embodiments, the inference result can also be evaluated for accuracy (e.g., measured using a confidence interval), and the unannotated data sample can be automatically labeled based on the inference result if the accuracy of the inference result exceeds a defined threshold. In some implementations, the automated annotation techniques can also include a metadata extraction technique wherein metadata associated with the unannotated data sample is extracted and evaluated to automatically apply an annotation to the unannotated data sample. For example, in implementations in which the machine learning model comprises a medical imaging diagnostic model and the unannotated data samples comprise medical images, the metadata extraction technique can involve extracting the clinical diagnosis from non-image-based data (e.g., radiology reports, physician notes, etc.) associated with the unannotated medical images.

The advanced annotation pipeline further includes a priority evaluation component that analyzes the unannotated data samples included in the annotation queue to facilitate determining how to prioritize annotating the unannotated data samples and/or what specific annotation technique or techniques to use to annotate the respective unannotated data samples based on predicted information gain and uncertainty in the machine learning model. In some embodiments, the priority evaluation component can estimate the confidence in the accuracy of an inference prediction that would be generated based on application of the machine learning model to the unannotated data samples (e.g., using inference dropout with prediction intervals estimated with Monte Carlo sampling, Bayesian deep networks, or the like). The priority evaluation component can further classify those unannotated data samples associated with a high confidence level (relative to a threshold confidence level) as low priority data samples and those unannotated data samples associated with a low confidence level (relative to a threshold confidence level) as high priority data samples. The advanced annotation pipeline can further include an annotation management component that assigns the unannotated data samples for annotation using one or more of the annotation techniques selected based on the estimated confidence or priority levels associated therewith. For example, in some embodiments, the annotation management component can send the unannotated data samples associated with a high confidence level, (or a low priority level), for annotation using an automated annotation technique (e.g., semi-supervised learning and/or metadata extraction), and send the unannotated data samples associated with low a confidence level (or high priority level) for annotation via manual review and labeling.

In various implementations, because manual annotation generally results in accurate annotations (minus human error), the manually annotated data samples can be added to the unannotated training data samples. In this regard, unannotated data samples included in the annotation queue that are associated with poor model performance can be identified and prioritized for manual annotation to ensure accurate annotated training data samples are generated for these types of data samples. Likewise, unannotated data samples included in the annotation queue that are associated with poor model performance can be considered to be well represented or already represented in the existing training data set. Accordingly, manual annotation of these high confidence unannotated data samples can consider a lower priority and thus these high confidence unannotated data samples can be prioritized for annotation via one or more of the more efficient/lower cost automated annotation techniques.

The advanced annotation pipeline can further employ an active learning process to evaluate the accuracy of the applied annotations and to learn correlations between data sample attributes and the accuracy of performance of the machine learning model to facilitate prioritizing unannotated data samples for annotation. For example, in various embodiments, the advanced annotation pipeline can include an annotation accuracy evaluation component that determines or predicts a confidence level in the accuracy of an annotation applied to an unannotated data sample using one or more of the annotation techniques described herein (e.g., using inference dropout with prediction intervals estimated with Monte Carlo sampling, Bayesian deep networks, or the like). The confidence computation method employed by the annotation accuracy evaluation component to determine a level of confidence in the accuracy of an applied annotation can vary based on what is available and/or the type of annotation technique/method used to apply the annotation. For example, in some implementations of semi-supervised based annotation wherein the inferencing model itself is used to generate an annotation for a data sample, the confidence in the applied annotation also be computed using the model itself. The inferencing model itself can also be used to determine a level of confidence in an annotation applied using other techniques in association with an active validation process (e.g., described infra). In another example, for weak annotation techniques (e.g., metadata extraction or the like), the confidence can also be computed based on supporting positive and negative data. In another example, for manually (i.e., human) applied annotations, the confidence can be determined based on historical accuracy of the entity in association with annotating a particular type of image, disease, etc., self-reported by the annotator, determined based on collaborative review of the annotation by other experts, or the like.

In this regard, in some embodiments, the annotation accuracy evaluation component can apply the machine learning model to the unannotated data sample to generate an inference result and compare this inference result with the applied annotation to facilitate determining the accuracy of the annotation (measured in a confidence level in the accuracy of the annotation). The active learning component can further be configured to add the annotated data samples associated with a high confidence level (e.g., relative to a threshold confidence level) to the training data set for training and updating the machine learning model. The active learning component can also identify annotated data samples associated with low confidence levels and tag these data samples for additional review. In this regard, the active learning component can identify incorrect annotations based on association with a low confidence level (e.g., relative to a threshold confidence level). In some implementations, the active learning component can provide real-time feedback to a manual annotator identifying incorrect annotations to facilitate correcting the annotations in real-time. In other implementations, the active learning component can send annotated data samples associated with a low confidence level back to the annotation queue for re-annotating using a different annotation technique or a different entity in implementations in which the low confidence annotation was manually applied.

In addition, based on analysis of the determined confidence levels associated with the annotated data samples, the active learning component can learn correlations between data sample attributes and the accuracy of performance of the machine learning model. For example, the active learning component can identify certain types of attributes associated with annotated data samples that are consistently associated with low degrees of confidence in the accuracy of the applied annotations. The priority evaluation component can further employ learned correlations between attributes of data samples that are attributed to poor model performance to identify unannotated data samples included in the annotation queue with those attributes. The priority evaluation component can further classify these unannotated data samples as "high priority" for annotating using manual annotation to facilitate generating more accurate annotated training samples comprising those attributes for training the model.

Various embodiments of the disclosed subject matter are exemplified with respect to annotating medical images for input to a medical image analysis model. However, it should be appreciated that the disclosed techniques are not limited to the medical imaging domain and can be applied to facilitate annotating data samples for various type of machine learning models in various domains. One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 1000 that facilitates enhancing the efficiency and accuracy of annotating data samples for supervised machine learning algorithms in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a model development module 108 and an annotation pipeline module 112. The model development module 108 and the annotation pipeline module 112 can respectively be or include machine-executable components stored in memory (not shown) associated with the one or more machines (not shown). The memory can further be operatively coupled to at least one processor (not shown), such that the components (e.g., the model development module 108, the annotation pipeline module 112 and the components associated therewith), can be executed by the at least one processor to perform the operations described. Examples of said and memory and processor as well as other suitable computer or computing-based elements, can be found with reference to FIG. 15, and can be used in connection with implementing one or more of the systems or components shown and described in connection with FIG. 1 or other figures disclosed herein. System 100 further include one or more data sources 102, unannotated data samples 104, an annotated training data set 106, annotation accuracy and attribute correlation information 212, an annotation queue 114, high confidence annotated data samples 116, low confidence annotated data samples 118, and a machine learning model 110, referred to herein as model M1.

In various embodiments, the model development module 108 can facilitate training and/or optimizing one or more machine learning models (e.g., machine learning model 110, M1) using accurately annotated/labeled training data samples. For exemplary purposes, system 100 and (additional systems described herein) is described with reference to training and development of a single machine learning model M1. However, it should be appreciated that system 100 can be configured to train and develop a plurality of different machine models respectively tailored to different input data sets. In the embodiment shown, the annotated training data samples that are used by the model development module 108 to train and/or optimize the machine learning model M1 are included in a set of annotated training data samples, identified in system 100 as annotated training data set 106. The annotated training data set 106 can include annotated data samples that have been annotated/labeled with annotations/labels that are known or are expected to be correct or accurate (e.g., with respect to a defined level of accuracy). The annotated training data set 106 can be stored in a suitable data structure.

The annotation pipeline module 112 can provide an advanced annotation pipeline that facilitate efficiently generating and adding annotated training data samples to the annotated training data set 106. In this regard, in various embodiments, the annotation pipeline module 112 can collect or receive unannotated data samples 104 from one or more data sources 102 and store them in an annotation queue 114. For example, in some implementations, the unannotated data samples 104 can include medical images and the one or more data sources 102 can include internal and/or external imaging databases associated with one or more healthcare operating entities. With these implementations, the machine learning model M1 can include a DNN image analysis model configured to automatically generate an inference classification based on the medical images. For example, M1 can include a diagnostic model configured to diagnose presence or absence of a medical condition based on analysis of the input medical images. The collection of unannotated data samples 104 into the annotation queue 114 can be performed regularly or continuously over time as more and more data samples are provided by the one or more data sources 102.

The annotation pipeline module 112 can further facilitate annotating the unannotated data samples 104 included in the annotation queue using one or more annotation techniques. In various embodiments, the annotation pipeline module 112 can select one or more annotation techniques for application to the respective unannotated data samples from amongst a defined set of different annotation techniques that have different strengths and weaknesses. For example, the different annotation techniques can include a manual annotation technique that provides for generating highly accurate annotations yet at a high cost and relatively low efficiency. The different annotation techniques can also include one or more automated annotation techniques that facilitate applying machine generated annotations to the unannotated data samples with increased efficiency yet variable degrees of accuracy. For example, one automated annotation technique can include a semi-supervised machine learning technique wherein the annotation pipeline module 112 applies the current version of the machine learning model 110 to the unannotated data sample to generate the annotation. The different annotation techniques are described in greater detail infra with reference to FIGS. 2-4.

In various embodiments, the annotation pipeline module 112 can judiciously manage which of the unannotated data samples 104 get annotated and what annotation technique or techniques are applied to annotate them based on predicted information gain and observed uncertainty in the machine learning model M1. The annotation pipeline module 112 can further evaluate the accuracy of annotations applied to the unannotated data samples 104 using the one or more annotation techniques. For example, in some implementations, the annotation pipeline module 112 can determine a confidence value/level for an annotated data sample that reflects a degree of confidence in the accuracy of the applied annotation. The annotation pipeline module 112 can further identify those annotated data samples having annotations with high confidence levels based on their confidence levels exceeding a defined threshold level of confidence. In the embodiment shown, these annotated data samples are identified high confidence annotated data samples 116. In one or more embodiments, the annotation pipeline module 112 can add the high confidence annotated data samples 116 to the annotated training data set 106. The annotation pipeline module 112 can also identify those annotated data samples having annotations with low confidence levels based on their confidence levels being less than a defined threshold level of confidence. In the embodiment shown, these annotated data samples are identified low confidence annotated data samples 118. In some embodiments, the annotation pipeline module 112 can send the low confidence annotated data samples 118 back to the annotation queue 114 for additional review and processing (e.g., annotation using a different annotation technique or different entity in implementations in which the incorrect annotation was applied by a manual annotator).

In some embodiments, the annotated training data set 106 can include an initial set of annotated training data samples that can be used to initiate training and development of the machine learning model M1. For example, the initial annotated training data samples can include manually labeled/annotated data samples that are known to be accurate (e.g., providing ground truth examples). In some implementations, the annotation pipeline module 112 can facilitate generating this initial set of annotated training data examples. With these embodiments, after initial training and development of M1 on the initial training data set, the annotation pipeline module 112 can facilitate adding additional annotated training data samples to the annotated training data set 106 generated via the advanced annotation pipeline in accordance with the techniques described herein. For example, the annotation pipeline module 112 can facilitate generating and adding the high confidence annotated data samples 116 to the annotated training data set 106. In this regard, the annotation pipeline module 112 can facilitate increasing the size and distribution of the annotated training data set 106 over time. The model development module 108 can further use the high confidence annotated data samples 116 added to the annotated training data set 106 to further train and refine or optimize the machine learning model 110 (M1) model over time.

The machine learning model 110 (M1) can be or include essentially any type of supervised machine learning algorithm configured to generate inferences based on unannotated data samples (e.g., unannotated data samples 104). For example, the machine learning model M1 can be or include a support vector machine model, a linear regression model, a logistic regression model, a naïve Bayes model, a linear discriminant analysis model, a decision tree model, a k-nearest neighbor model, a neural network model, and the like. Various embodiments are exemplified wherein the machine learning model M1 corresponds to DNN model configured to generate inferences based on analysis of medical images (e.g., a DNN configured to diagnose presence or absence of a medical condition or disease reflected in the medical images). However, it should be appreciated that the machine learning model M1 can include other types of classification models in the healthcare domain as well as various non-healthcare domains.

In some embodiments, in addition to generating an inference based on an unannotated data sample, the machine learning model M1 can also be configured to determine a confidence value that represents the degree of confidence the model has in the accuracy of the inference output. For example, in an implementation in which the machine learning model M1 is configured to diagnose presence or absence of a medical condition reflected in an input medical image, the machine learning model M1 can also be configured to generate a confidence value/score for the diagnosis that indicates the level of confidence the model has in the accuracy of the diagnosis (e.g., Diagnosis=yes, condition A present; Confidence=89%).

Figure 2:
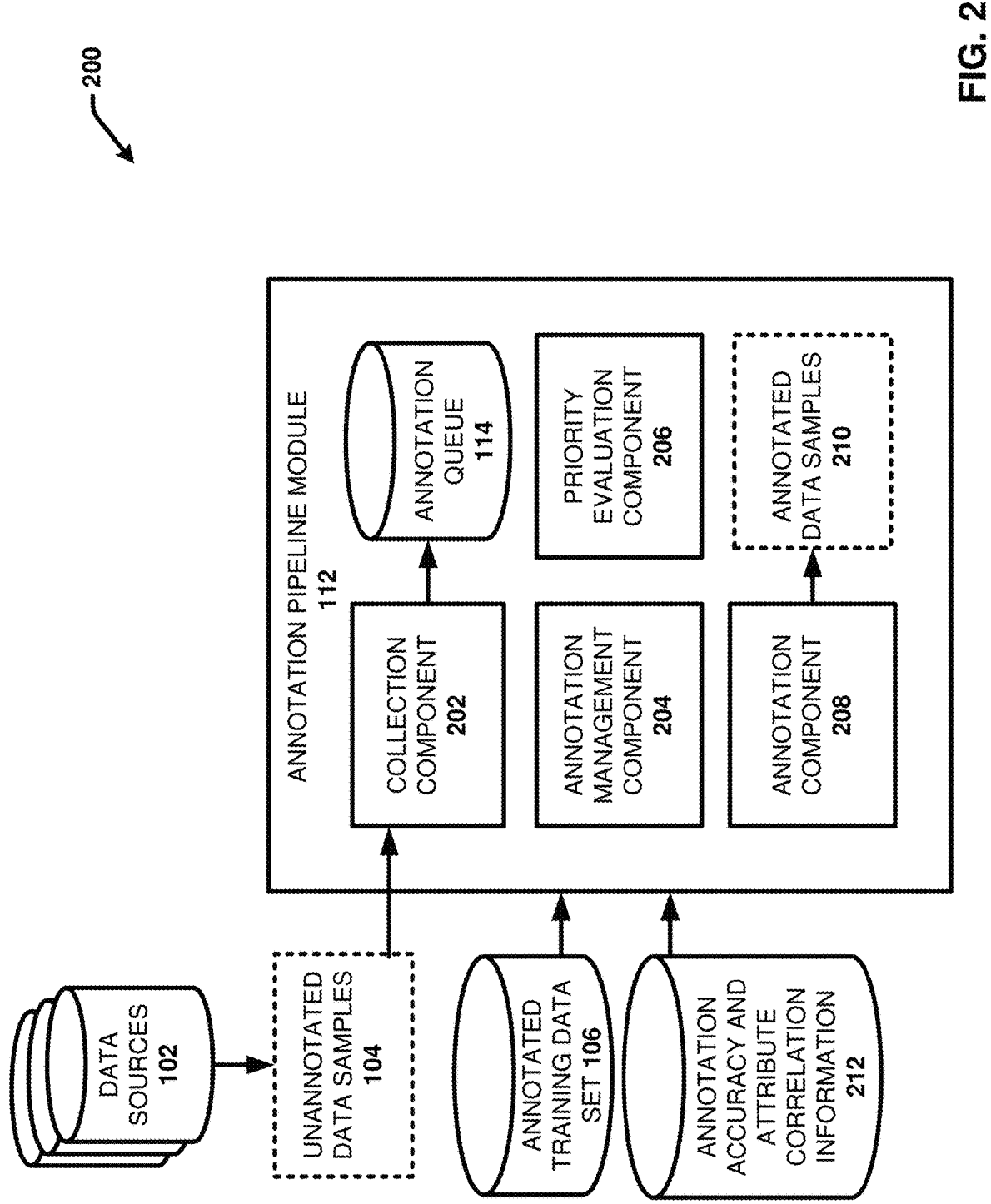
FIG. 2 illustrates a block diagram of another example, non-limiting system that facilitates enhancing the efficiency and accuracy of annotating data samples for supervised machine learning algorithms in accordance with one or more embodiments of the disclosed subject matter.

FIG. 2 illustrates a block diagram of another example, non-limiting system 200 that facilitates enhancing the efficiency and accuracy of annotating data samples for supervised machine learning algorithms in accordance with one or more embodiments of the disclosed subject matter. In one or more embodiments, system 200 is a subsystem of system 100. In this regard, system 100 can include system 200, and vice versa. Repetitive description of like elements employed in respective embodiments is omitted for sake of brevity.

In one or more embodiments, in addition to the annotation queue, the annotation pipeline module 112 can include collection component 202, priority evaluation component 206, annotation management component 204, and annotation component 208. The collection component 202 can collect or receive the unannotated data samples 104 from the one or more data sources 102 and store the unannotated data samples 104 in the annotation queue. For instance, in association with application of system 200 to annotate medical images for training a DNN model to diagnose a medical condition based on analysis of medical images, the collection component 202 can collect or receive hundreds to thousands to millions (or more) of unannotated medical images for the particular type of medical condition from various medical institutions and for various different patient groups/populations to establish a comprehensive set of the possible representations of the different image-based variables that can indicate presence and absence of the medical condition. In accordance with this example, the one or more data sources can include picture archiving and communication systems (PACS)s, medical image acquisition devices, and other types of data sources that provide the medical images.

In some embodiments, the unannotated data samples 104 can also be associated with additional information that identifies or indicates various relevant attributes associated with the respective unannotated data samples that can facilitate evaluating the unannotated data samples to determine the inference about the data samples that the machine learning model is configured to infer. In some implementations of these embodiments, the collection component 202 can collect this additional relevant information for the unannotated data samples 104 from the one or more data sources 102 and associate this additional relevant information with the respective unannotated data samples in the annotation queue 114. In other implementations of these embodiments, this additional relevant information can be pre-associated with the respective unannotated data samples 104 when collected as metadata.

For example, in implementations in which the unannotated data samples 104 comprise medical images, the medical images can be associated with related, non-image-based, clinical information for the respective images that can facilitate automatically annotating the images (e.g., using M1, a metadata extraction technique, and/or another automated technique). For instance, the related, non-image-based clinical information can include information that identifies or indicates a diagnosis reflected in the medical image taken from text and/or audio data sources associated with the medical image, such as but not limited to: radiology reports, clinical notes, pathology reports, clinical dictations, physician's orders, laboratory reports, pathology reports, electronic medical records (EMR) for the patient from which the image was taken, and the like. For example, the non-image-based clinical information can include diagnosis (DX) codes, current procedural terminology (CPT) codes, prescription (Rx) codes, International Classification of Disease (ICD) codes, relative value unit (RVU) codes, and the like. In another example, the non-image-based clinical information can include relevant clinical terms or phrases that identify or indicate a diagnosis reflected in the medical image extracted from clinical notes and/or reports using natural language processing (NLP) techniques.

The unannotated medical images can also be associated with additional, non-clinical information that can may be correlated to variances in model performance. For example, in some implementations, the non-clinical information associated with an unannotated medical image can include attributes regarding the patient from which the medical image was taken (e.g., patient medical history, patient comorbidity, patient demographics such as age, gender, location, height, weight, etc.), the image acquisition device (type, make, model, resolution, etc.), the image source (e.g., institution, geographic region, etc.), and the like, that can be correlated to variances in the performance of the diagnostic model. For instance, as described in greater detail infra with reference to FIG. 6, using an active learning process, the annotation pipeline module 112 can learn that the model consistently generates low confidence diagnosis for medical images of a specific patient subgroup (e.g., age group, gender, location, etc.), or for medical images from a specific geographic region. These learned correlations can be used to prioritize selection of new images included in the annotation queue 114 from that subgroup or geographic region for annotation using manual annotation (or another high accuracy annotation technique) to facilitate generating more accurately annotated training images for that subgroup or geographic region for training and optimizing the performance of the model on images from that subgroup or geographic region.

The annotation management component 204 can evaluate the unannotated data samples (e.g., unannotated medical images) collected in the annotation queue 114 to determine how to prioritize annotating the unannotated data samples and/or to determine the most appropriate mechanism or mechanisms for annotating each (or in some implementations one or more) unannotated data sample based on one or more prioritization criteria. In this regard, the annotation pipeline module 112 can leverage different types of annotation techniques to facilitate annotating the data samples, wherein the different types of annotation techniques can vary with respect to the amount of time and resources involved. For example, in one implementation, the different types of annotation techniques can include a manual annotation technique, a metadata extraction annotation technique and a semi-supervised machine learning technique. With the manual annotation technique, an unannotated data sample can be manually reviewed and labeled (e.g., by a radiologist viewing and interacting with the actual medical image). With the metadata extraction annotation technique, an unannotated data sample can be automatically annotated based on machine analysis of the associated metadata (e.g., the additional, non-image-based clinical information associated with a medical image) that identifies or indicates the classification of the unannotated data sample that the machine learning model (e.g., M1) is configured to infer. With the semi-supervised machine learning technique, the machine learning model itself (e.g., M1) can be applied to the unannotated data sample to generate an inference output and this inference output can be applied as the annotation/label for the data sample. In various embodiments, as discussed in greater detail infra, the annotation component 208 can perform or facilitate performing the different annotation techniques to generate the corresponding annotations/labels for the unannotated data samples.

In this regard, in one or more embodiments, the annotation management component 204 can evaluate the unannotated data samples 104 included in the annotation queue 114 to determine which annotation technique or techniques from among the different annotation technique options to apply to each (or in some implementations one or more) unannotated data sample included in the annotation queue 114 based on one or more prioritization criteria. In some implementations, the annotation management component 204 can further recommend the selected annotation techniques for application by a system manager. For example, the annotation management component 204 can generate annotation prioritization information that identifies the annotation technique or techniques selected for each (or in some implementations one or more) of the unannotated data samples. The annotation management component 204 can further provide the prioritization information to an entity that controls annotation of the unannotated data samples to facilitate managing annotation of the unannotated data samples by the entity. For example, the annotation management component 204 can facilitate rendering the prioritization information at a device associated with a user responsible for managing and/or controlling annotation of the unannotated data samples. The user can then choose whether to accept and implement the annotation technique or techniques selected for each (or in some implementations one or more) unannotated data sample based on their domain knowledge. In other implementations, the annotation management component 204 can directly manage and/or control annotation of the unannotated data samples (e.g., using the annotation component 208) based on the prioritization information. For example, in some embodiments, the annotation management component 204 can send the respective unannotated data samples to the annotation component 208 for annotation using the specific annotation technique or techniques selected for the respective unannotated data samples.

Accordingly, rather than sending every single unannotated data sample for annotation via manual review, the annotation management component 204 can employ the prioritization criteria to determine which of the unannotated data samples to select or recommend for manual annotation and which to send to select or recommend for annotation using an alternative annotation technique. In some implementations, the annotation management component 204 can also select more than one annotation techniques for annotating an unannotated data sample. The annotation management component 204 can also employ the prioritization criteria to determine a priority order for annotating the respective unannotated data samples via the one or more of the annotation techniques. The annotation management component 204 can further generate and provide an entity with information recommending application of the priority order and/or directly send the unannotated data samples to the annotation component 208 for annotation in accordance with the priority order. In another implementation, the annotation management component 204 can employ the prioritization information to select only a subset of the unannotated data samples for annotating, wherein the remaining unselected unannotated data samples can be removed or discarded from the annotation queue 114. For example, rather than selecting all of the unannotated data samples that are added to the annotation queue for annotation using one or more of the annotation techniques, the annotation management component 204 can select only a subset of the most relevant/useful data samples for annotating, wherein the most relevant or useful data samples are determined based on the prioritization criteria. The annotation management component 204 can further generate and provide an entity with information recommending the subset for annotation and/or directly send only the selected subset to the annotation component 208 for annotation.

In one or more embodiments, the prioritization criteria can include an expected degree of confidence in the accuracy of the inference output that would be generated by the machine learning model (e.g., M1) based on application of the machine learning model to the unannotated data sample. For example, assuming the machine learning model comprises a medical image diagnostic model, the prioritization criteria can include an expected degree of confidence that the diagnostic model will accurately diagnose presence or absence of a particular medical condition based on the input image. A low expected degree of confidence associated with a particular unannotated data sample indicates the machine learning model needs more training on annotated training data samples that correspond to the particular unannotated data sample to improve the accuracy of the machine learning model towards those types of data samples. Thus, in various embodiments, the annotation management component 204 can favor prioritization of annotating unannotated data samples associated with low expected degrees of confidence in a manner that results in increasing the amount of accurately annotated training data samples of that type. In this regard, the annotation management component 204 can prioritize time and resources for annotating data samples based on how important the data samples are for improving the accuracy and/or specificity of the model.

For example, in some embodiments, the annotation management component 204 can prioritize the unannotated data samples associated with low estimated confidence levels, (referred to generally as low confidence unannotated data samples), for annotating and/or annotating using a more robust annotation technique relative to other annotation techniques (e.g., manual annotation as opposed to automated annotation) over the unannotated data samples associated with high estimated confidence levels, (referred to as high confidence unannotated data samples). For instance, the annotation management component 204 can select or recommend the manual annotation technique for unannotated data samples having an estimated degree of confidence that is below a threshold degree of confidence. Likewise, the annotation management component 204 can select or recommend an automated annotation technique (e.g., the semi-supervised annotation technique and/or the metadata extraction technique) for unannotated data samples having an estimated degree of confidence that is above a threshold degree of confidence. In another implementation, the annotation management component 204 can select or recommend annotation using a combination of two or more different annotation techniques for data samples exhibiting a defined excepted level of confidence. For example, the annotation management component 204 can select or recommend annotation using two automated annotation techniques (e.g., the semi-supervised annotation technique and the metadata extraction technique) for unannotated data samples having an estimated degree of confidence that is above a first threshold degree of confidence and below a second threshold degree of confidence (e.g., medium confidence data samples). In another example, the annotation management component 204 can select or recommend application of both the manual and automated annotation techniques for unannotated data samples having extremely low estimated degree of confidence (e.g., relative to a defined threshold). In another implementation, the annotation management component 204 can select or recommend lower confidence unannotated data samples for annotating before higher confidence unannotated data samples. In another implementation, the annotation management component 204 can select or recommend only a subset of the unannotated data samples included in the annotation que for annotation (e.g., using any of the annotation techniques) based on association with an estimated degree of confidence that is below a threshold degree of confidence.

In some embodiments, the annotation pipeline module 112 can include priority evaluation component 206 to determine the expected degree of confidence in the accuracy of the inference output that would be generated by the machine learning model (e.g., M1) based on application of the machine learning model to each (or in some implementations one or more) unannotated data sample of the unannotated data samples. With these embodiments, the priority evaluation component 206 determine the expected degree of confidence using machine learning and/or statistical analysis (e.g., using inference dropout with prediction intervals estimated with Monte Carlo sampling, Bayesian deep networks, etc.) of the annotated training data set 106 and/or annotation accuracy and attribute correlation information 212.

For example, in some embodiments, the priority evaluation component 206 can determine the expected degree of confidence for the respective unannotated data samples based on learned correlations between data sample attributes and the accuracy of performance of the machine learning model on previous data samples comprising the attributes. With these embodiments, (as described in greater detail infra with reference to the annotation component 208 and the active learning component 502), the annotation component 208 can facilitate applying annotations to unannotated data samples included in the annotation queue using one or more of the available annotation techniques, resulting in a transformation of the unannotated data samples into annotated data samples 210. The annotation pipeline module 112 can further include an active learning component (e.g., active learning component 502) that evaluates the accuracy of the applied annotations and determines estimated degrees of confidence in the accuracy of the applied annotations. Based on the evaluated accuracy of the applied annotations, the active learning component can learn correlations between data sample attributes (e.g., image-based attributes and/or non-image-based attributes from associated metadata in implementations in which the data samples are images) and the levels of confidence in the accuracy of the performance of the machine learning model (M1). The active learning component can further generate and store correlation information regarding these learned correlations in a suitable data structure. For example, in the embodiment shown, this learned correlation information is identified as annotation accuracy and attribute correlation information 212. The priority evaluation component 206 can further employ these learned correlations to estimate the expected level of confidence in the accuracy of inference results that would be generated by the machine learning model (M1) based on application to the new unannotated data samples included in the annotation queue with same or similar attributes.

In other implementations, the priority evaluation component 206 can compare the unannotated data samples to the annotated training data samples included in the annotated training data set 106 (e.g., which are expected to be or determined to be accurate) to estimate the degrees of confidence in an inference result generated based on application of the machine learning model (M1) to the unannotated data samples. With these implementations, the priority evaluation component 206 can estimate the degree of confidence in the accuracy of an inference result for an unannotated data sample based on a degree of similarity between the unannotated data sample and one or more annotated training data samples included in the annotated training data set 106. For example, in implementations in which the input data samples are images (e.g., medical images) the priority evaluation component 206 can compare correspondences between image-based and/or non-image-based features of the unannotated image and respective annotated images included in the annotated training data set 106. In this regard, the higher the degree of correspondence, the greater the confidence level in the expected accuracy of the machine learning model (M1) on the unannotated data sample.

In accordance with these embodiments, the priority evaluation component 206 can evaluate each (or in some implementations one or more) unannotated data sample included in the annotation queue 114 to determine the expected degree of confidence in the accuracy of the inference output that would be generated by the machine learning model (e.g., M1) based on application of the machine learning model to the unannotated data sample. The expected degree of confidence can be measured using various suitable valuation schemes. For example, in some implementations, the expected degree of confidence can be measured as a percentage, wherein the higher the percentage the greater the degree of confidence. In another example implementation, the expected degree of confidence can be measured using a suitable scale (e.g., 1, 2, or 3, wherein 1=low confidence, 2=medium confidence, and 3=high confidence).

In some embodiments, the prioritization criteria can also include a quantity of annotated training data samples included in the training data set that were used to train the machine learning model that correspond to an unannotated data sample included in the annotation queue. For example, in various implementations, after the machine learning model is initially trained on a set of annotated training data samples, new types of unannotated data samples (e.g., with different attributes/representations) can be received the were not included and/or were underrepresented in the initial training data set. As a result, the model will likely not be able to accurately evaluate those types of data samples. Thus in various embodiments, the annotation management component 204 can prioritize unannotated data samples that are missing from or underrepresented in the annotated training data set 106 for annotation and/or annotation using a more robust annotation technique (e.g., manual review as opposed to an automated annotation technique) to ensure accurate training examples are generated and added to the annotated training data set 106 for training and updating the machine learning model.

With these embodiments, the priority evaluation component 206 can evaluate an unannotated data sample included in the annotation queue in view of the existing annotated training data samples included in the annotated training data set 106 to determine a degree to which the unannotated data sample is represented in the training data set. For example, the priority evaluation component 206 can determine a percentage of the amount annotated training data samples included in the annotated training data set 106 that correspond to the unannotated data sample (e.g., using a feature to feature comparison). The annotation management component 204 can further prioritize annotating unannotated data samples that are associated with a lower representation percentage (e.g., relative to a threshold percentage) over unannotated data samples that are associated with a higher representation percentage (e.g., relative to a threshold percentage). For example, the annotation management component 204 can select or recommend lower representation percentage data samples for annotating before higher representation percentage data samples. In another example, the annotation management component 204 can select or recommend lower representation percentage data samples for annotating using a first annotation technique (e.g., manual annotation), and higher representation percentage data samples for annotating using a second annotation technique (e.g., an automated annotation technique).

In another implementation, the prioritization criteria can include predefined prioritization information that defines or indicates the specific annotation technique or techniques to apply and/or the annotation order for specific types of data samples (e.g., with specific attributes). For example, a system administrator can classify data samples associated with a specific patient subgroup, geographic region, medical condition, data sample source, etc., with priority information that defines or indications the specific annotation technique or techniques to apply and/or the annotation order for specific types of data samples (e.g., with specific attributes). In some implementations, the priority information can include a defined annotation priority level for the specific type of data sample. For example, in some implementations, the annotation priority levels can include two levels; "low priority" and "high priority." In another implementation, the annotation priority levels can include three levels: "low priority," "medium priority," and "high priority." In another example, the annotation priority levels can include any number of priority levels on a scale of 1 to N, wherein the higher the number N, the higher the priority level.

With these implementations, regardless of the scale employed, the annotation management component 204 can be configured to determine how to prioritize annotating the unannotated data samples and/or which annotation technique or techniques to apply based on the annotation priority levels associated with the respective unannotated data samples. In various implementations, the annotation management component 204 can be configured to favor annotation for higher priority level data samples over lower priority data samples. For example, the annotation management component 204 can select or recommend higher priority data samples for annotating before lower priority data samples. In another example, the annotation management component 204 can select or recommend higher priority data samples for annotating using a first annotation technique (e.g., manual annotation), and lower priority data samples for annotating using a second annotation technique (e.g., an automated annotation technique). Accordingly, a system administrator can classify a particular type of data sample with a high priority level to facilitate selection of unannotated data samples included in the annotation queue 114 of that type for annotating using manual annotation and/or annotating before other data samples in order to tailor generating a set of annotated training data samples for that particular data sample subgroup to optimize model performance for that subgroup and/or to generate a tailored version of the model for that that subgroup. In this regard, the prioritization criteria can include predefined or learned information regarding what types of data samples are most important/relevant for annotating and/or annotating with manual annotation based on the goals and needs of the entity applying the machine learning model so as to facilitate tailoring generating of accurate training examples for tailoring the performance of the machine learning model in accordance with those goals and needs In some embodiments, the priority evaluation component 206 can determine the annotation priority levels for the respective the unannotated data samples included in the annotation queue 114 based on the prioritization criteria. For example, the priority evaluation component 206 can determine a priority level for an unannotated data sample based on the estimated degree of confidence in the inference output that would be generated based on application of the machine learning model to the unannotated data sample. The priority evaluation component 206 can also determine the priority level based on the amount (e.g., a percentage) of training data samples included in the annotated training data set 106 that correspond to the unannotated data sample. In another implementation, the priority evaluation component 206 can determine the annotation priority level as a function of a combination of the estimated degree of confidence and the amount. According to these embodiments, the priority evaluation component 206 can employ a prioritization scoring scheme wherein the lower the estimated degree of confidence, the higher the priority level, and/or the lower the amount of corresponding annotated training data samples, the higher the priority level. For example, the priority evaluation component 206 can assign unannotated data samples included in the annotation queue 114 associated with a low estimated degree of confidence (e.g., relative to a threshold degree of confidence) with a "high priority level." Likewise, the priority evaluation component 206 can assign unannotated data samples included in the annotation queue 114 associated with a high estimated degree of confidence (e.g., relative to a threshold degree of confidence) with a "low priority level." The annotation management component 204 can further determine how to prioritize annotating the unannotated data samples and/or select the specific annotation technique for applying to the respective unannotated data sample based on the associated priority level, as discussed above. For instance, the annotation management component 204 can select or recommend the high priority unannotated data samples for annotation via manual review and the low priority unannotated data samples for annotation via an automated annotation technique (e.g., the metadata extraction annotation technique and/or the semi-supervised machine learning technique).

The annotation component 208 can facilitate applying the one or more selected annotation techniques to the respective unannotated data samples to generate annotations for the respective unannotated data samples, thereby transforming the unannotated data samples into annotated data samples 210. The applied annotations can be associated with the data samples as metadata, embedded on or within the data sample (e.g., embedded on a medical image), associated with the data samples as an auxiliary data file, or in another suitable manner. In this regard, in implementations in which the annotation technique comprises an automated annotation technique, the annotation component 208 can apply or perform the automated annotation technique to generate the corresponding annotation. For example, the annotation component 208 can perform a metadata annotation technique and evaluate the metadata associated with an unannotated data sample to determine the target annotation (e.g., a diagnosis in implementations in which the data sample comprises a medical image and the machine learning model M1 is configured to infer the diagnosis). The annotation component 208 can also perform a semi-supervised machine learning technique to generate the annotation. In this regard, the annotation component 208 can apply the machine learning model itself (e.g., M1) to the unannotated data sample to generate an inference output. The annotation component 208 can further apply this inference output to the data sample as the annotation/label for the data sample.

In other implementations in which the annotation technique comprises a manual annotation technique, the annotation component 208 can facilitate providing the unannotated data sample to a manual annotator in association with a request to apply a manual annotation. The annotation component 208 can also receive the annotated version of the unannotated data sample with the manually applied annotation. For example, in one embodiment, the annotation component 208 can include and/or interface with a manual annotation application that presents one or more manual annotators (humans) with unannotated (or in some implementations previously annotated) data samples for annotation. For instance, in implementations in which the data samples comprise medical images, the annotation application can provide for rendering the unannotated medical images to a manual annotator (e.g., a radiologist) and receiving user input from the manual annotator that identifies or indicates a desired evaluation of the medical image (e.g., a diagnosis, a severity level, a disease or condition classification, etc.). The annotation application can further generate and apply an annotation or label to the medical image based on the user input, resulting in a transformation of the medical image to an annotated medical image. The annotation application can further provide the annotated medical image to the annotation pipeline module 112 for further processing.

In various embodiments the initial distribution of unannotated cases to a particular annotation technique by the annotation management component 204 could be random, determined manually, or based on some other criteria determined as a result of an active learning process (e.g., this image falls into the patient group/category of images we have determined to be high priority or low priority based on the model M1 demonstrating poor performance toward that type of image and/or based on a determination that that type of image is a new type of image or otherwise outside the training data set). As described in greater detail infra with reference to FIG. 6, as the active learning process progresses over time, the continued distribution of new, unannotated data cases collected in the annotation que 114 can become more automated with (e.g., with no manual intervention. For example, as a result of the active learning processes, if the system 200 (i.e., the priority evaluation component 206) thinks M1 will generate an annotation for the "unannotated" case with a high confidence level, then this case can be ranked with a lower priority and thus sent for annotation using an automated annotation technique (e.g., a semi-supervised annotation technique and/or a metadata extraction technique). On the other hand, if the system thinks M1 will generate an annotation for the "unannotated" case with a low confidence level, then this case can be ranked with a higher priority and thus sent for manual annotation.

Figure 3:
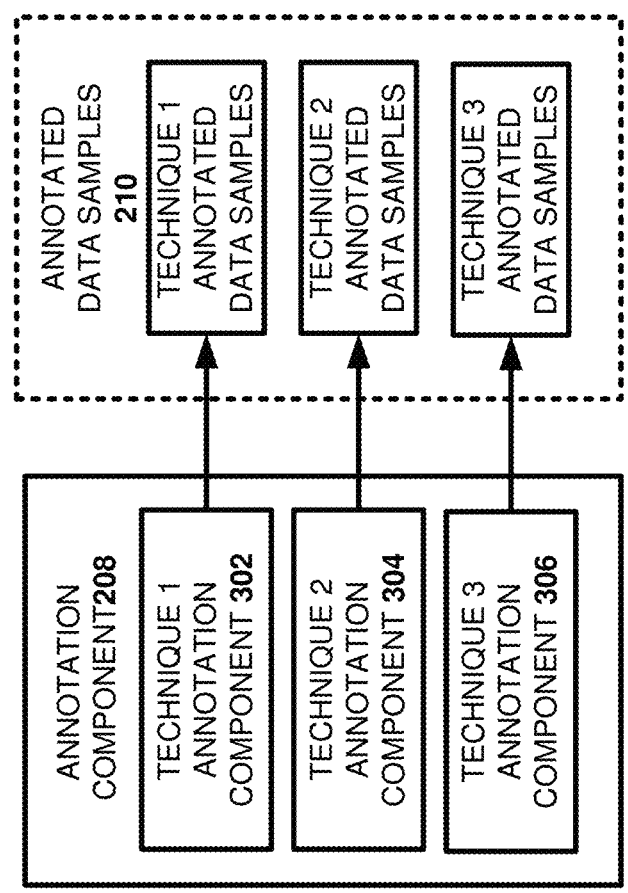
FIG. 3 illustrates an example annotation component and associated annotated data samples provided by the annotation component in accordance with one or more embodiments of the disclosed subject matter.

FIG. 3 illustrates an example annotation component 208 and associated annotated data samples provided by the annotation component in accordance with one or more embodiments of the disclosed subject matter. Repetitive description of like elements employed in respective embodiments is omitted for sake of brevity.

In some embodiments, the annotation component 208 can include a plurality of annotation sub-components, wherein each annotation sub-component is configured to perform or apply a different annotation technique to an unannotated data sample. For example, in the embodiment shown, the annotation sub-components are identified as annotation technique 1 component 302, annotation technique 2 component 304, and annotation technique 3 component 306. It should be appreciated that three annotation sub-components are shown merely for exemplary purposes and that the number of annotation sub-components can include or more less than three. Each of the different annotation sub-components further generates a different subset of annotated data samples. For example, in the embodiment shown, the annotated data samples 210 include a first subset of annotated data samples generated via annotation technique 1, a second subset of annotated data samples generated via annotation technique 2, and a third subset of annotated data samples generated via annotation technique 3.

Figure 4:
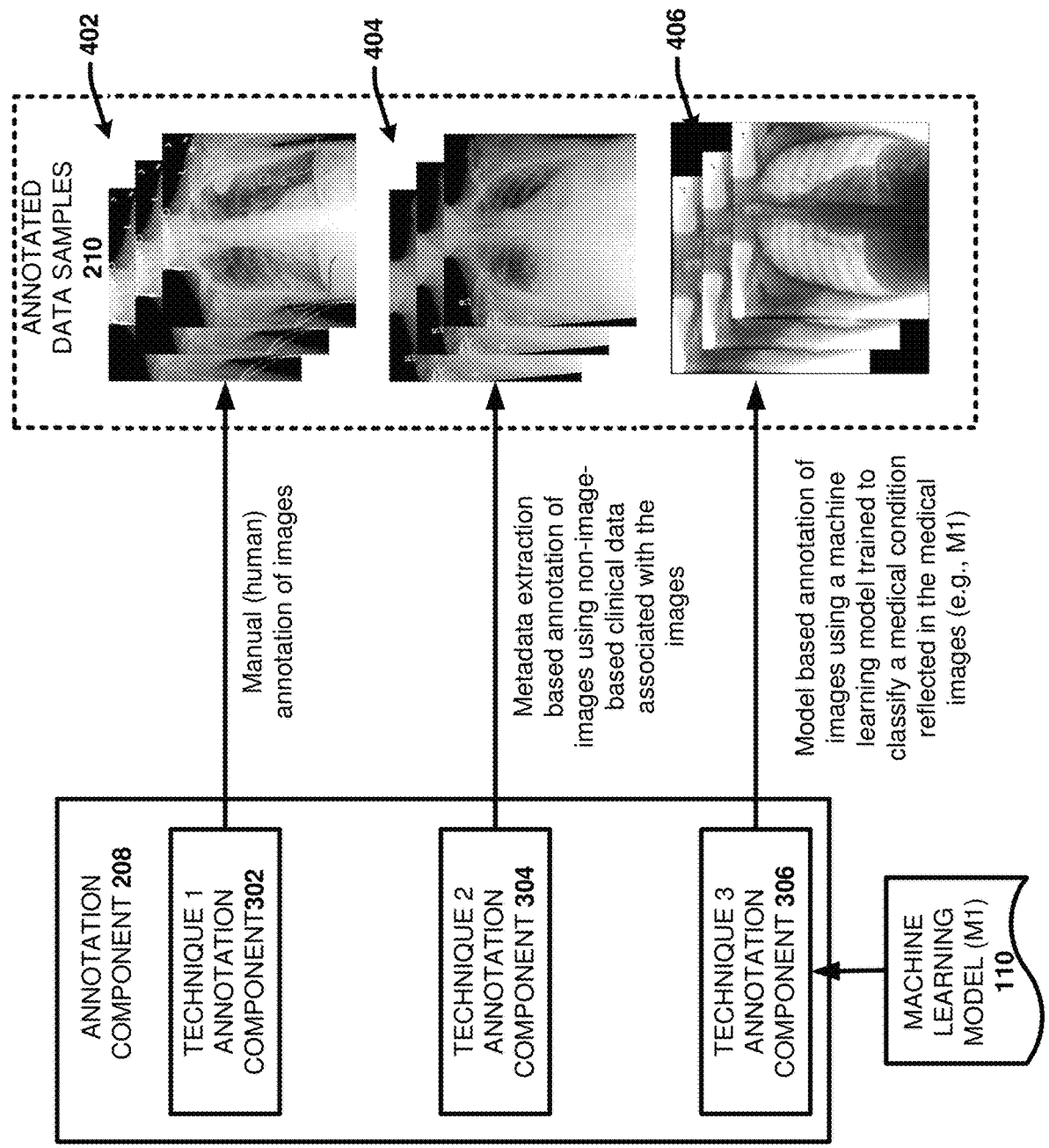
FIG. 4 illustrates example subsets of annotated data samples generated by the annotation component in association with application to medical images in accordance with one or more embodiments of the disclosed subject matter.

FIG. 4 illustrates example subsets of annotated data samples generated by the annotation component 208 in association with application to medical images in accordance with one or more embodiments of the disclosed subject matter. Repetitive description of like elements employed in respective embodiments is omitted for sake of brevity.

In the embodiments shown, each of the annotation sub-components (e.g., annotation technique 1 component 302, annotation technique 2 component 304, and annotation technique 3 component 306) are configured to facilitate applying annotations to medical images using a different annotation technique. For example, the technique 1 annotation component 302 can be configured to facilitate applying manual annotations to the medical images, resulting in generation of a first subset 402 of manually annotated medical images. The technique 2 annotation component 304 can be configured to perform a metadata extraction technique to generate a second subset 404 of automatically annotated medical images. For example, the technique 2 annotation component 304 can access and evaluate non-image-based clinical data (e.g., DX codes, Rx codes, key terms included in clinical notes/reports, etc.) associated with each unannotated image selected for annotation via technique 2 to determine and apply an annotation each medical image (e.g., a diagnosis, a disease/condition classification, etc.), resulting in generation of a first subset 402 of manually annotated medical images. The technique 3 annotation component 306 can be configured to perform a model-based annotation technique to generate a third subset 406 of automatically annotated medical images. For example, in some implementations, the technique 3 annotation component 304 can access and apply the machine learning model (M1) to the unannotated medical images to generate an inference result that machine learning model has been trained to generate. The technique 3 annotation component 306 can further annotate or label the medical image with the inference result.

Figure 5:
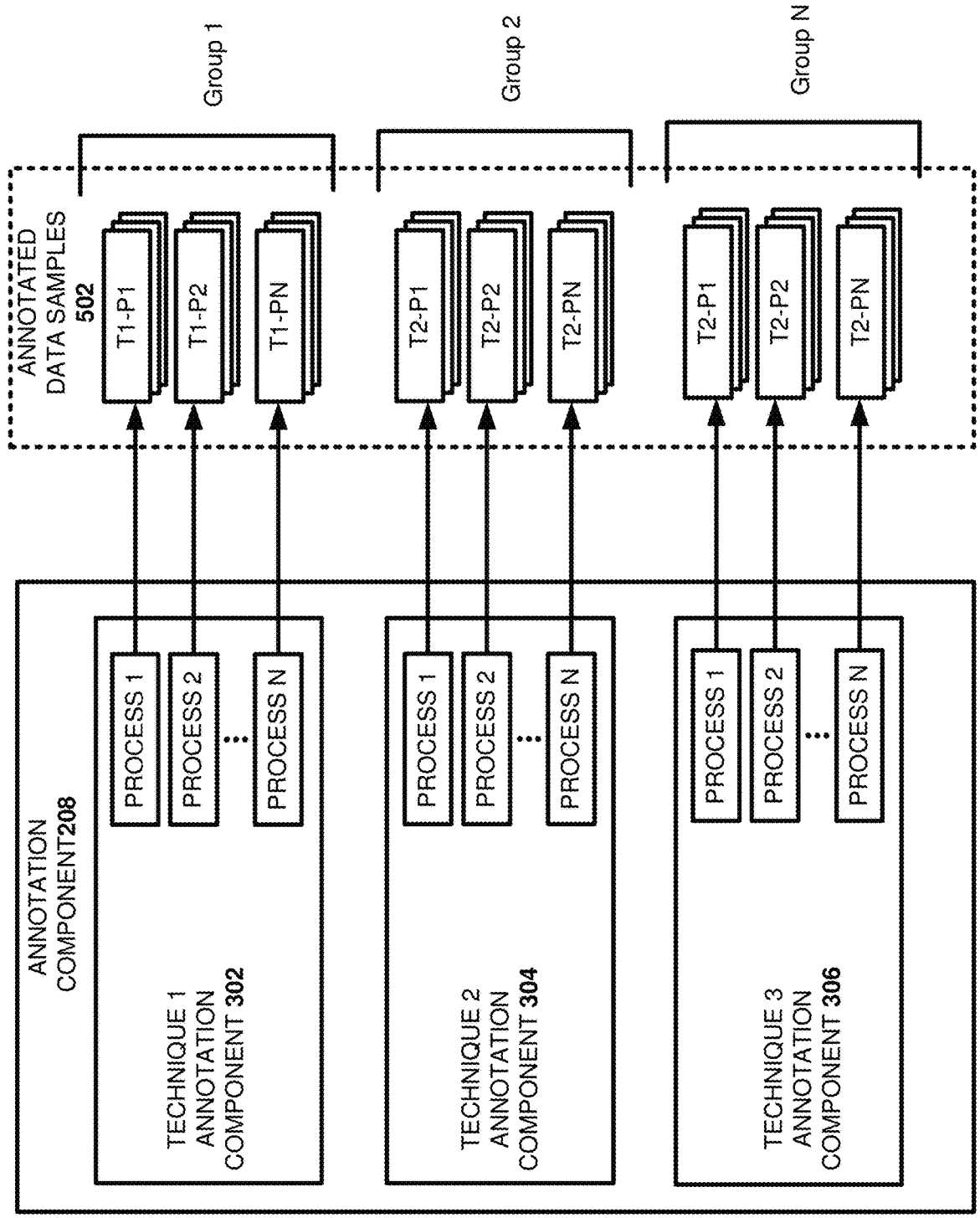
FIG. 5 illustrates another example annotation component and associated annotated data samples provided by the annotation component in accordance with one or more embodiments of the disclosed subject matter.

FIG. 5 illustrates another example annotation component 208 and associated annotated data samples 502 provided by the annotation component in accordance with one or more embodiments of the disclosed subject matter. Repetitive description of like elements employed in respective embodiments is omitted for sake of brevity.

In some embodiments, each individual annotation technique provided by the respective annotation components (e.g., technique 1 annotation component 302, technique 2 annotation component 304, technique 3 annotation component 306, etc.) can have multiple algorithms/models or entities (e.g. people in implementations in which the annotation technique involves manual annotation) that execute or perform annotations. For example, in the embodiment shown in FIG. 5, each annotation component and associated annotation technique can include a plurality of different annotation processes (e.g., process 1, process 2, process N, etc., wherein N is an integer). Each annotation process can involve the same annotation technique yet vary with respect to one or more factors. For example, in some implementations, the different annotation processes associated with a same annotation technique can vary with respect to the model or algorithm used. In another example, the different annotation processes associated with a same annotation technique can vary with respect to the entity that performs the annotation process (e.g., a person, an organization, a system, a device, etc.). In this regard, each different annotation process (e.g., algorithm/model, entity, etc.) that involves the same annotation technique algorithm or person can vary with respect to the level of accuracy of the resulting annotations. The accuracy can be modeled built based on the performance on previous annotations and domain knowledge. For example, with respect to medical images, the accuracy of different annotation algorithms and/or entities that perform a same or similar annotation technique to medical images can vary based on factors such as disease or organ being annotated, the person's or algorithm's specialization (e.g., a neuroradiologist will be better at diagnosing something in their expertise, like stroke or hemorrhage, than a muscular skeletal problem like bone cancer). Accordingly, from this model of accuracy, the disclosed techniques can compute a confidence level for each annotation that is performed by the different annotation processes (e.g., algorithms/models and/or entities) associated with a same annotation technique.

In this regard, a data sample (e.g., an image) can be annotated more than once using different annotation techniques and/or different annotation processes associated with a same annotation technique. For example, as shown in FIG. 5, the resulting annotated data samples 502 can include several groups (e.g., group 1, group 2, group N) of data samples corresponding to the same input sample yet annotated using different annotation techniques. Within each group, the annotated data samples can include subsets of the same data sample respectively annotated with a different annotation process (e.g., algorithms/models and/or entity), wherein each annotation process can vary with respect to the level of accuracy of the annotations generated based on the sample being annotated. For example, for each annotation processe 1-N that employs annotation technique 1, the annotated data samples can include a first subset of annotated data samples annotated using technique 1 and process 1 (T1-P1), a second subset of annotated data samples annotated using technique 2 and process 2 (T1-P1), and so on. In various embodiments, an annotated data sample (e.g., an image) can be only be submitted for training after the aggregated confidence levels for the multiple annotations applied exceeds a specified threshold level of confidence. In another embodiment, the confidence level associated with each annotation generated for a same data sample can be used as a weighting factor during algorithm training (e.g., training of M1).

Figure 6:
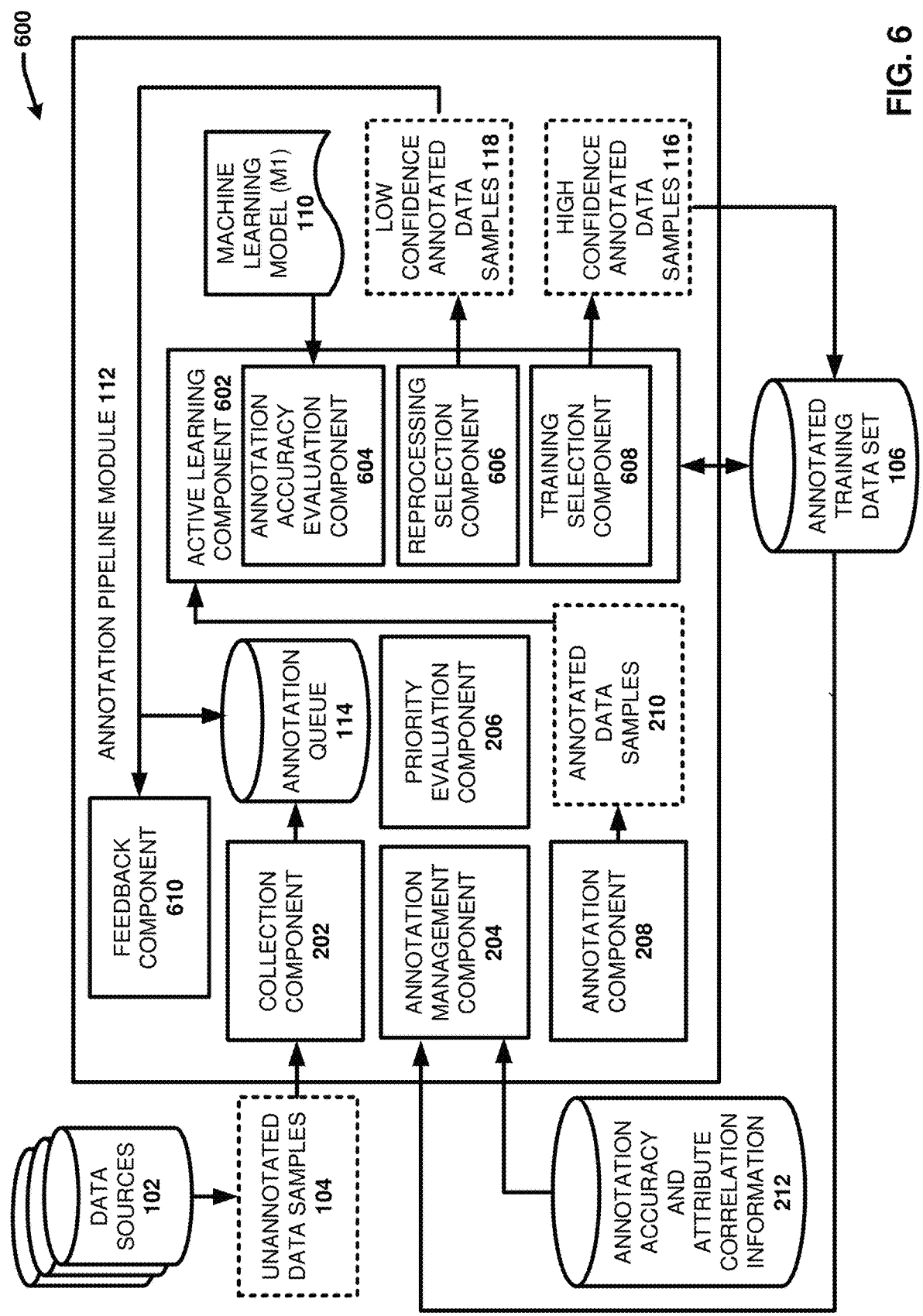
FIG. 6 illustrates a block diagram of another example, non-limiting system that facilitates enhancing the efficiency and accuracy of annotating data samples for supervised machine learning algorithms in accordance with one or more embodiments of the disclosed subject matter.

FIG. 6 illustrates a block diagram of another example, non-limiting system 600 that facilitates enhancing the efficiency and accuracy of annotating data samples for supervised machine learning algorithms in accordance with one or more embodiments of the disclosed subject matter. In one or more embodiments, system 600 is a subsystem of system 100. In this regard, system 100 can include system 600, and vice versa. System 600 includes same or similar features and functionalities as system 200 with the addition of the active learning component 602 and the feedback component 610 to the annotation pipeline module 112. Repetitive description of like elements employed in respective embodiments is omitted for sake of brevity.

In various embodiments, the active learning component 602 can employ an active learning process to assess the accuracy of the annotations applied to the unannotated data samples using the different annotation techniques. The active learning component 602 can also employ the active learning process to facilitate identifying and correcting annotation errors (e.g., identifying incorrect annotations). In this regard, the active learning component 602 can include annotation accuracy evaluation component 604, reprocessing selection component 606 and training selection component 608.

The annotation accuracy evaluation component 604 can evaluate the annotated data samples 210 to determine an estimated degree of accuracy of the applied annotations. In various embodiments, the estimated degree of accuracy in the applied annotations can be measured or expressed using a confidence interval. In this regard, similar to the estimated degree of confidence in the accuracy of the expected inference result determined by the priority evaluation component 206 prior to annotation of the respective unannotated samples, the annotation accuracy evaluation component 604 can further perform a confidence evaluation of actual annotations generated/applied to a data sample using one or more of the annotation techniques/processes described herein. The confidence computation method employed by the annotation accuracy evaluation component 604 to determine a level of confidence in the accuracy of an applied annotation can vary based on what is available and/or the type of annotation technique/method used to apply the annotation. For example, in some implementations of semi-supervised based annotation wherein the inferencing model (M1) is used to generate an annotation for a data sample, the confidence in the applied annotation also be computed using the model (M1). The inferencing model itself can also be used to determine a level of confidence in an annotation applied using other techniques in association with an active validation process. In another example, for weak annotation techniques (e.g., metadata extraction or the like), the annotation accuracy evaluation component 604 can determine the confidence in an applied annotation based on supporting positive and negative data. In another example, for manually (i.e., human) applied annotations, the annotation accuracy evaluation component 604 can determine the confidence in the applied annotation based on historical accuracy of the entity in association with annotating a particular type of image, disease, etc., and/or based on collaborative review of the annotation by other experts. In another example, manually applied annotations can be received with self-reported confidence estimates provided by the annotator that reflect the degree of confidence the annotator has in the accuracy of their applied annotation.

The confidence estimates determined for the applied annotations can be measured using various suitable valuation schemes. For example, in some implementations, the annotation accuracy evaluation component 604 can measure the estimated degree/level of confidence in the accuracy of an applied annotation as a percentage, wherein the higher the percentage the greater the degree/level of confidence. In another example implementation, the estimated degree/level of confidence can be measured using a suitable scale (e.g., 1, 2, or 3, wherein 1=low confidence, 2=medium confidence, and 3=high confidence). In some embodiments, the estimated degree/level of confidence (determined prior to annotation) and the determined degree/level of confidence in the accuracy of the applied annotation can be expressed using the same valuation scheme.

In some embodiments, the annotation accuracy evaluation component 604 can be configured to assume all manually annotated data samples are accurately annotated. With these embodiments, the annotation accuracy evaluation component 604 can associate a high degree/level of confidence (e.g., a defined high degree of confidence) to the manually annotated data samples and forgo additional processing to calculate a specific confidence level for the manually annotated data samples. With these embodiments, the annotation accuracy evaluation component 604 can focus on evaluating the estimated degree/level of confidence in the accuracy of annotations applied using alternative techniques (e.g., metadata extraction annotation, semi-supervised annotation, and the like. In other embodiments, the annotation accuracy evaluation component 604 can evaluate the accuracy of all of the annotated data samples 210, including the manually annotated data samples. The annotation accuracy evaluation component 604 can employ various techniques to determine the estimated degree/level of confidence in the accuracy of an applied annotation, which can vary depending on the annotation technique employed to apply/generate the annotation.

For example, in some embodiments, the machine learning model M1 itself can be configured to generate both an inference output and a confidence measure that represents the degree of confidence the model has in the accuracy of the inference output. With these embodiments, for those unannotated data samples that are processed using the semi-supervised machine learning annotation technique, the machine learning model M1 can be applied to generate both an inference output and a confidence level that reflects the degree of confidence the model has in the accuracy of the inference output. Because the inference output is used as the annotation, the degree of confidence will correspond to the degree of confidence in the accuracy of the applied annotation.

In some embodiments in which the machine learning model M1 is configured to generate an inference output and a confidence value corresponding to the level of confidence in the inference output, the machine learning model M1 can also be applied to data samples annotated using techniques other than the semi-supervised machine learning technique to determine the degree of confidence in the accuracy of the applied annotation. For example, the annotation accuracy evaluation component 604 can apply the machine learning model M1 to a manually annotated data sample and/or a metadata annotated data sample to generate an inference output and a confidence level in the accuracy of the inference output. The annotation accuracy evaluation component 604 can further compare the manually/metadata applied annotation to the inference output. In some implementations, if the manually/metadata applied annotation and the inference output are the same, the annotation accuracy evaluation component 604 can apply the machine learning model determined confidence level to the manually/metadata applied annotation. The annotation accuracy evaluation component 604 can also employ this technique to identify inaccurate manual and/or metadata applied annotations. For example, if the inference output and the manual/metadata applied annotation are different and the machine learning model confidence level in the inference output is high (e.g., relative to a threshold degree of confidence), the annotation accuracy evaluation component 604 can consider the manual/metadata applied annotation incorrect and associate a low degree of confidence with the manual/metadata applied annotation.

In some implementations, if the inference output and a manually applied annotation are different and the machine learning model confidence level in the inference output is low (e.g., relative to a threshold degree of confidence), the annotation accuracy evaluation component 604 can consider the manually applied annotation to be more correct than the inference output under the assumption that manual annotations are generally highly accurate (e.g., 80-90% accurate). The annotation accuracy evaluation component 604 can further disregard the confidence level provided by the machine learning model and associate a high level of confidence with the manual applied annotation. For example, the high level of confidence can be a predetermined level of confidence. In other implementations, if the inference output and the manual/metadata applied annotation are the same and the machine learning model confidence level in the inference output is low (e.g., relative to a threshold degree of confidence), the annotation accuracy evaluation component 604 can consider the correspondence an indication that the machine learning model M1 should increase its confidence valuation of the inference output. With these scenarios, the annotation accuracy evaluation component can 604 can be configured to increase the confidence level in the accuracy of the manual/metadata applied annotation by a defined amount.

In other embodiments, the annotation accuracy evaluation component 604 can compare the annotated data samples 210 to the annotated training data samples included in the annotated training data set 106 (e.g., which are expected to be or determined to be accurate) to estimate the degree of confidence in the applied annotations. With these embodiments, the annotation accuracy evaluation component 604 can compare an annotated data sample (e.g., annotated using any of the different annotation techniques) to the annotated training data samples included in the annotated training data set 106 to identify one or more annotated training data samples that correspond to the annotated data sample (e.g., using a feature to feature comparison). For example, in implementations in which the data samples are medical images, the annotation accuracy evaluation component 604 can find annotated training images included in the annotated training data set 106 that match or substantially correspond to (e.g., with respect to a defined threshold of correspondence) a newly annotated medical image annotated using any of the different annotation techniques. The annotation accuracy evaluation component 604 can further consider the annotation applied to the unannotated data sample to be correct if the annotation corresponds to (e.g., is the same as) the annotations associated with the corresponding annotated training data samples. Likewise, the annotation accuracy evaluation component 604 can consider the annotation applied to the unannotated data sample to be incorrect if the annotation corresponds to (e.g., is the same as) the annotations associated with the corresponding annotated training data samples. In accordance with these embodiments, the annotation accuracy evaluation component 604 can determine the level of confidence in the accuracy of an applied annotation based on the number of corresponding training data samples with annotations that match the applied annotation. In this regard, the greater the number, the higher the degree of confidence.

Regardless of the technique employed to determine the level of accuracy of an applied annotation or level/degree of confidence in the accuracy of the applied annotation, in various embodiments, the training selection component 608 can be configured to identify the high accuracy or high confidence level annotated data samples for adding to the annotated training data set 106. For example, the training selection component 608 can identify and/or select the annotated data samples having annotations with estimated confidence levels that exceed a threshold confidence level. In the embodiment shown, these data samples are identified as the high confidence annotated data samples 116. The training selection component 608 can further add the high confidence annotated data samples to the annotated training data set 106 for training and/or updating the machine learning model by the model development module 108.

In addition, the reprocessing selection component can further identify annotated data samples (from amongst the annotated data samples 210) associated with a low estimated degree of confidence in the accuracy of the applied annotations. For example, the reprocessing selection component 606 can identify those annotated data samples (from amongst the annotated data samples 210) that are determined to have annotations associated with a confidence level that is below a threshold confidence level. In the embodiment shown, these data samples are identified as low confidence annotated data samples 118. In some implementations, the reprocessing selection component 606 can classify these low confidence annotated data samples 118 as incorrect. In various embodiments, the reprocessing selection component 606 can further select the low confidence annotated data samples 118 for reprocessing through the advance annotation pipeline. In this regard, the reprocessing selection component 606 can select the annotated data samples from amongst the annotated data samples 210 that are incorrectly annotated or are likely to be incorrectly annotated and send them back to the annotation queue for receiving additional annotation.

In some implementations, the reprocessing selection component 606 can further associate historical annotation information with the respective low confidence annotated data samples 118 added back to the annotation queue 114. For example, the historical annotation information can identify the annotation technique used to generate the respective low confidence annotations. In some implementations, the historical annotation information can also specify the specific confidence level determined for annotations (e.g., a percentage value or the like). In some implementations in which the annotation technique was a manual annotation technique, the reprocessing selection component 606 can also associate information with the annotated data sample identifying the specific annotator or group of annotators that applied the manual annotation. In association with re-processing or re-annotating a low confidence annotated data sample, the existing annotation can be removed or kept associated with the data sample.

The annotation management component 204 can further prioritize and/or select one or more annotation technique for re-annotating a low confidence annotated data sample based in part on the historical annotation information associated therewith. For example, in some embodiments, the priority evaluation component 206 can classify the low confidence annotated data samples 118 added back to the annotation queue 114 as high priority level data samples (e.g., relative to a defined priority level classification scheme or threshold). The annotation management component 204 can further prioritize the data samples for annotation according to their priority level as discussed supra. For example, the annotation management component 204 can select or recommend annotating the high priority data samples for annotation via manual annotation as opposed to an automated annotation technique. The specific method selected for reprocessing or re-annotating a low confidence annotated data sample added back to the annotation queue 114 can also be based on the annotation technique or technique applied that resulted in generation of the low confidence annotation. For example, in some implementations, the annotation management component 204 can be configured to select a different annotation technique over the previously applied annotation technique that resulted in the low confidence annotation. Similarly, if the annotation technique was a manual annotation technique, the annotation management component 204 can recommend or send the low confidence data sample for annotation via a different annotator or group of annotators. In another implementation, the annotation management component 204 can select the specific annotation technique for re-annotating a low confidence annotated data sample based on the specific degree of confidence associated therewith. For example, the annotation management component 204 can employ different thresholds of review that correspond to different degree of confidence. In this regard, if an annotated data sample has degree of confidence that is less than a first threshold but above a second threshold, then the annotation management component 204 can select a first annotation technique or combination of annotation techniques for re-annotating the data sample. However, if the annotated data sample has a degree of confidence that is less than the second threshold, then the annotation management component 204 can select a second annotation technique for re-annotating the data sample.

The annotation pipeline module 112 can also include a feedback component 610 that can generate feedback information regarding the incorrectly annotated data sample and facilitate rendering the feedback information at a device associated with an entity (e.g., a system administrator, an expert reviewer, etc.) responsible for reviewing the incorrect annotations. For example, the example, the feedback component 610 can notify a system administrator or another appropriate entity (e.g., the manual annotator or annotation team) regarding identified annotated data samples with annotations associated with low confidence levels (e.g., relative to a threshold confidence level). In this regard, the feedback component 610 can generate a notification regarding an identified low confidence data sample and present the notification to the system administrator. The notification can include the historical annotation information, and/or the specific degree of confidence determined for the annotation. In accordance with these embodiments, the system administrator (or another appropriate entity) can receive real-time feedback regarding incorrect annotations. The system administrator can further take appropriate action to correct the incorrect annotations and/or ensure similar data samples are correctly annotated in the future via the advance annotation pipeline.

Figure 7:
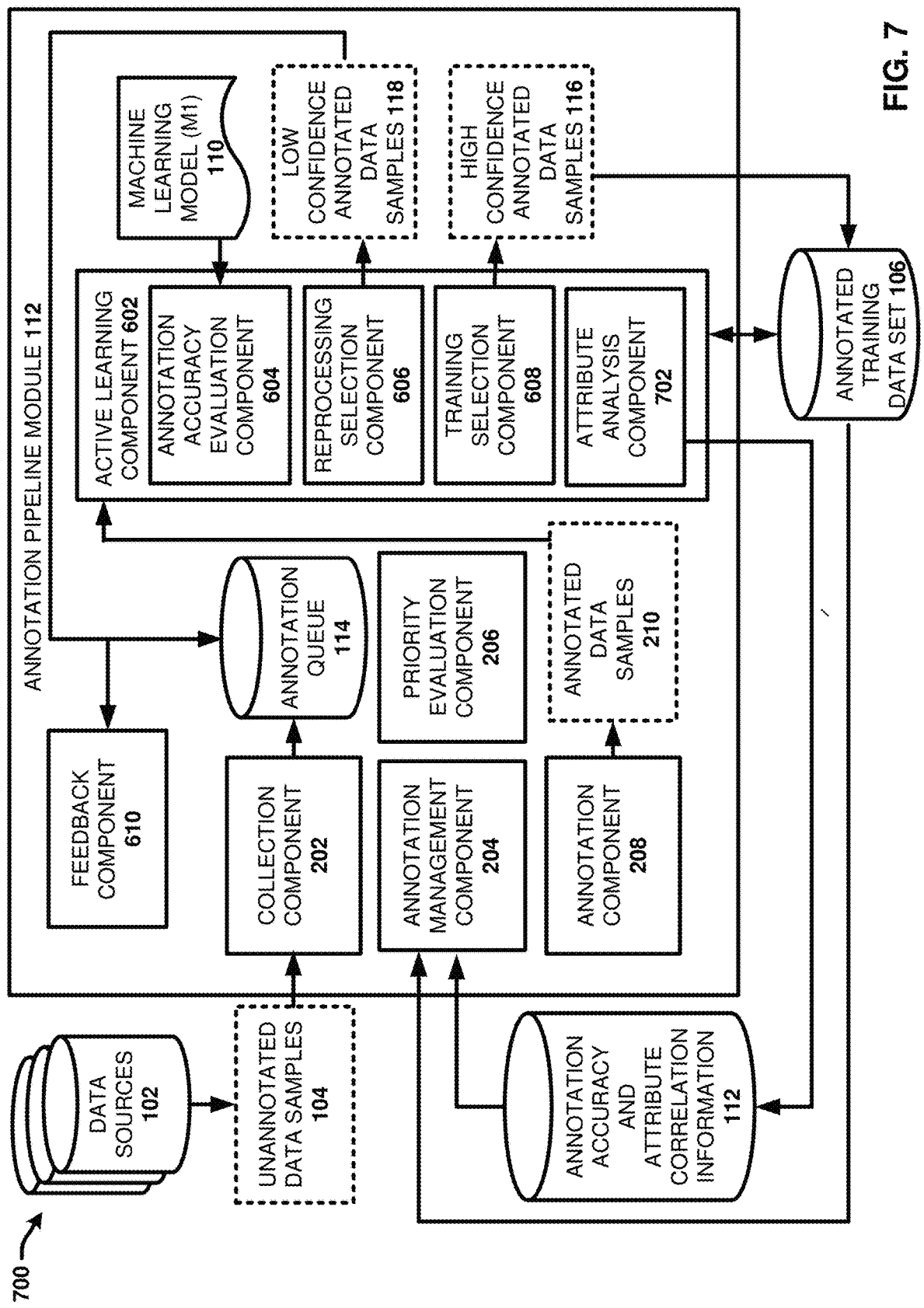
FIG. 7 illustrates a block diagram of another example, non-limiting system that facilitates enhancing the efficiency and accuracy of annotating data samples for supervised machine learning algorithms in accordance with one or more embodiments of the disclosed subject matter.

FIG. 7 illustrates a block diagram of another example, non-limiting system 700 that facilitates enhancing the efficiency and accuracy of annotating data samples for supervised machine learning algorithms in accordance with one or more embodiments of the disclosed subject matter. In one or more embodiments, system 700 is a subsystem of system 100. In this regard, system 100 can include system 700, and vice versa. System 700 includes same or similar features and functionalities as system 600 with the addition of attribute analysis component 702 to the active learning component 602. Repetitive description of like elements employed in respective embodiments is omitted for sake of brevity.

In some embodiments, the active learning component 602 can further include an attribute analysis component 702 to learn correlations between data sample attributes and accuracy of performance of the machine learning model M1. In this regard, the attribute analysis component 702 can generate and/or regularly update the annotation accuracy and attribute correlation information 212 as new correlations between data sample attributes and the accuracy of the performance of the machine learning model M1 is learned over time. For example, the attribute analysis component 702 can employ one or more machine learning and/or statistical analysis techniques to learn correlations and/or patterns regarding what type of data samples or sample attributes are consistently associated with inaccurate and accurate model predictions based on the annotated data samples generated via the semi-supervised machine learning annotation technique. In this regard, the attribute analysis component 702 can correlate the estimated confidence level in the accuracy of the inference result generated via the semi-supervised machine learning technique to the level of accuracy of the machine learning model toward that particular data sample and/or specific attributes associated with that particular data sample. For example, with respect to medical images, the attribute analysis component 702 can learn that the machine learning model M1 exhibits poor or strong performance for images associated with a particular patient subgroup (e.g., grouped by age, gender, or another criterion), a particular geographic region, or the like. The attribute analysis component 702 can employ the same confidence evaluation generated in association with application of the machine learning model to data samples annotated using other annotation techniques to learn correlations between the accuracy of the performance of the machine learning model M1 to specific data samples or data sample attributes. The attribute analysis component 702 can similarly evaluate the estimated confidence levels in the accuracy of applied annotations to learn correlations between data sample types and/or data sample attributes that are consistently associated with accurate and inaccurate annotations. For example, with respect to medical images, the attribute analysis component 702 can learn that images associated with a particular patient subgroup (e.g., grouped by age, gender, or another criterion), a particular geographic region, or the like, consistently receive inaccurate or accurate annotations, consistently receive inaccurate or accurate annotations via a specific annotation technique, and the like.

In various embodiments, the priority evaluation component 206 can further employ the annotation accuracy and attribute correlation information 212 to determine priority levels for the unannotated data samples 104 (e.g., as new unannotated data samples are collected over time). For example, the priority evaluation component 206 can determine higher priority levels for data sample types and/or data samples with certain attributes that are associated with poor model performance and/or inaccurate annotation. When determining the priority levels, the priority evaluation component 206 can further account for the average level/degree of confidence/accuracy determined for the data sample type (e.g., with one or more specific attributes), the amount of data samples of that type that are received and associated with poor model performance and/or inaccurate annotations, and/or the frequency with which those types of data samples are associated with poor model performance and/or inaccurate annotations. Likewise, the priority evaluation component 206 can determine lower priority levels for data sample types and/or data samples with certain attributes that are associated with strong model performance and/or accurate annotations. The priority evaluation component 206 can similarly account for the average level/degree of confidence/accuracy determined for the data sample type (e.g., with one or more specific attributes), the amount of data samples of that type that are received and associated with strong model performance and/or accurate annotations, and/or the frequency with which those types of data samples are associated with strong model performance and/or accurate annotations.

The annotation management component 204 can further prioritize annotation of the unannotated data samples and/or selection of the specific annotation technique or techniques for annotating the unannotated data samples based on their priority levels in accordance with the techniques described herein. In this regard, the annotation management component 204 can identify specific unannotated data samples included in the annotation queue 114 that should be annotated using manual review to ensure accurate training data samples are generated for the sample representation. For example, with respect to medical images, the priority evaluation component 206 can classify unannotated medical images associated with a particular patient subgroup or geographic region with high priority levels based on learned correlation/accuracy information that indicates these types of medical images are associated with poor model performance and/or inaccurate annotations. The annotation management component can further use this information to prioritize sending unannotated images received in the annotation queue for that particular patient subgroup or geographic region for manual annotation to generate more accurate training examples for that patient subgroup or geographic region. Likewise, the attribute analysis component 702 can learn correlations/patterns regarding what type of data samples or sample attributes are consistently associated with accurate model predictions to identify specific unannotated data samples included in the annotation queue that no longer need manual annotation (e.g., because the model has consistently demonstrated accurate evaluation of these types of unannotated data samples) and thus can be excluded from annotation or annotated using an alternative, automated annotation technique. As a result, the annotation pipeline can significantly reduce the amount of time and cost associated with annotating training data samples for training and optimization of the machine learning model.

Figure 8:
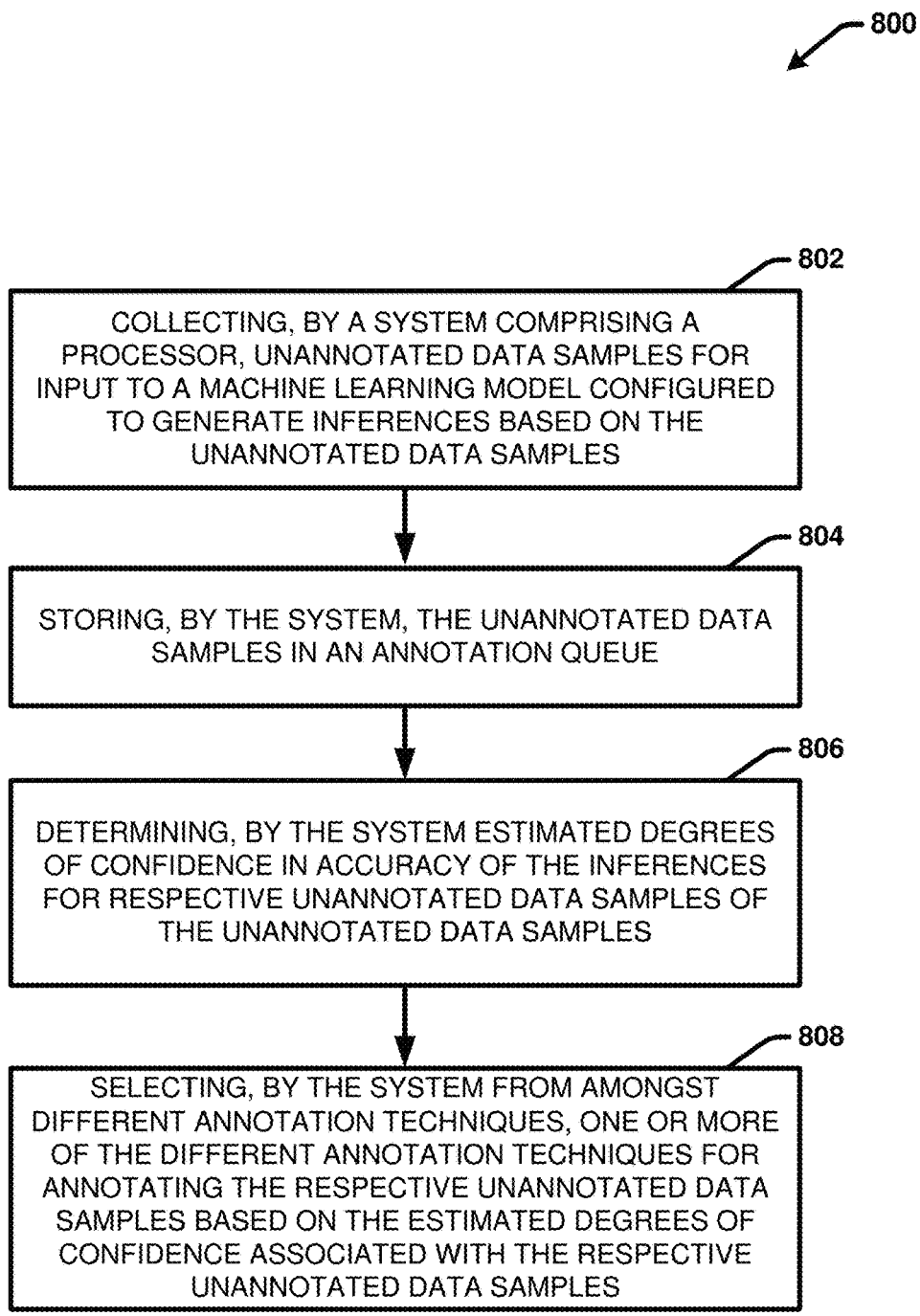
FIG. 8 provides a flow diagram of an example, non-limiting computer-implemented method that facilitates annotating data samples for supervised machine learning algorithms in accordance with one or more embodiments of the disclosed subject matter.

FIG. 8 provides a flow diagram of an example, non-limiting computer-implemented method 800 that facilitates annotating data samples for supervised machine learning algorithms in accordance with one or more embodiments of the disclosed subject matter. Repetitive description of like elements employed in respective embodiments is omitted for sake of brevity.

At 802, a system comprising a processor (e.g., system 100, system 200, system 600, system 700, or the like) can collect (e.g., via collection component 202) unannotated data samples (e.g., unannotated data samples 104) for input to a machine learning model configured to generate inferences based on the unannotated data samples (e.g., machine learning model 110, M1). At 804, the system can store the unannotated data samples in an annotation queue (e.g., annotation queue 114). At 806, the system can determine estimated degrees of confidence in accuracy of the inferences for respective unannotated data samples of the unannotated data samples (e.g., via priority evaluation component 206). At 808, the system can further select, from amongst different annotation techniques, one or more of the different annotation techniques for annotating the respective unannotated data samples based on the estimated degrees of confidence associated with the respective unannotated data samples (e.g., via annotation management component 204).

Figure 9:
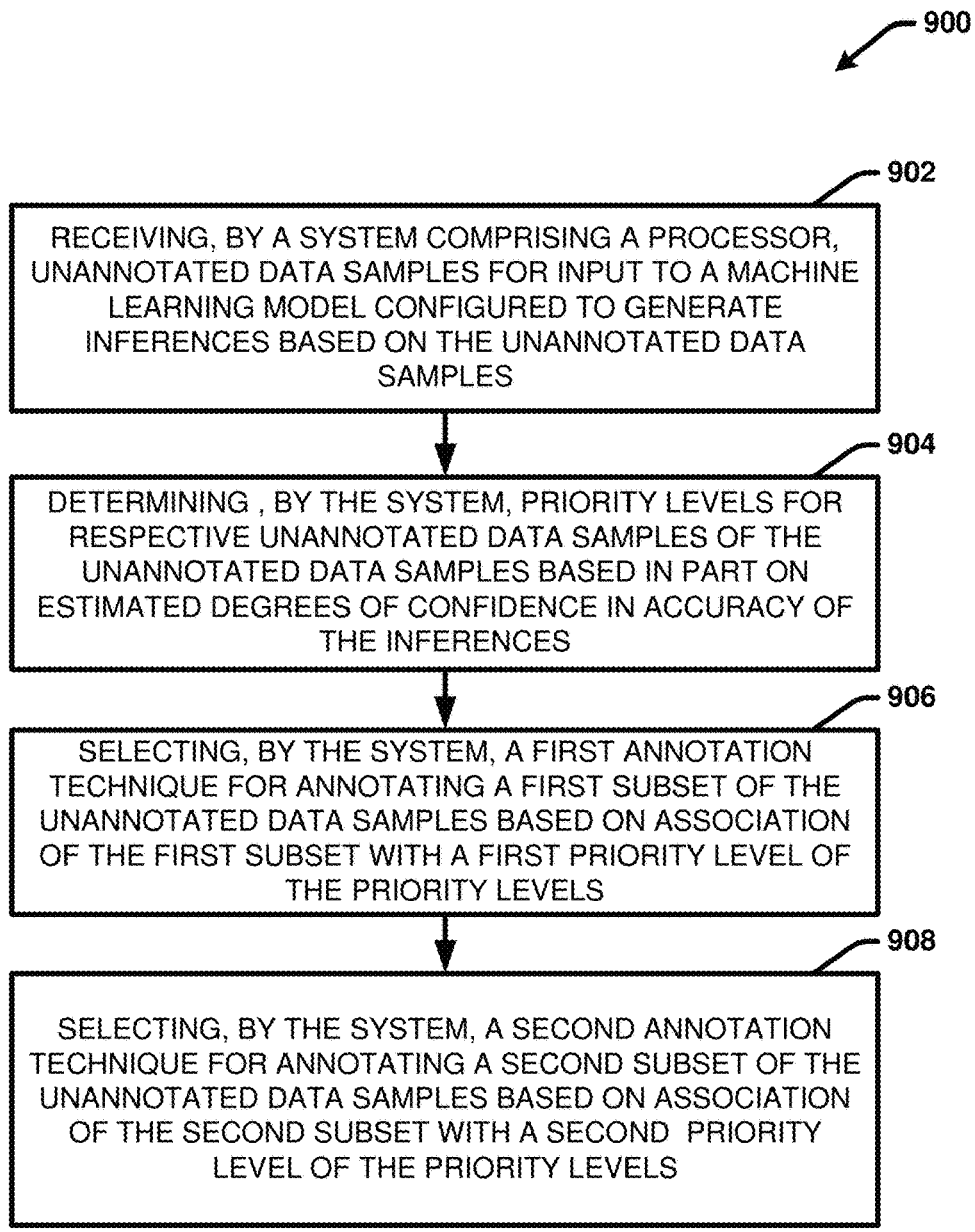
FIG. 9 provides a flow diagram of another example, non-limiting computer-implemented method that facilitates annotating data samples for supervised machine learning algorithms in accordance with one or more embodiments of the disclosed subject matter.

FIG. 9 provides a flow diagram of another example, non-limiting computer-implemented method 900 that facilitates annotating data samples for supervised machine learning algorithms in accordance with one or more embodiments of the disclosed subject matter. Repetitive description of like elements employed in respective embodiments is omitted for sake of brevity.

At 902, a system comprising a processor (e.g., system 100, system 200, system 600, system 700, or the like) can receive (e.g., via collection component 202) unannotated data samples (e.g., unannotated data samples 104) for input to a machine learning model configured to generate inferences based on the unannotated data samples (e.g., machine learning model 110, M1). At 904, the system can determine priority levels for respective unannotated data samples of the unannotated data samples based in part on the estimated degrees of confidence in accuracy of the inferences (e.g., via priority evaluation component 206). At 906, the system can select, a first annotation technique (e.g., a manual annotation technique) for annotating a first subset of the unannotated data samples based on association of the first subset with a first priority level (e.g., a high priority level relative to a defined threshold) of the priority levels (e.g., via annotation management component 204). At 908, the system can further select, a second annotation technique (e.g., an automated annotation technique) for annotating a second subset of the unannotated data samples based on association of the second subset with a second priority level (e.g., a low priority level relative to a defined threshold) of the priority levels (e.g., via annotation management component 204).

Figure 10:
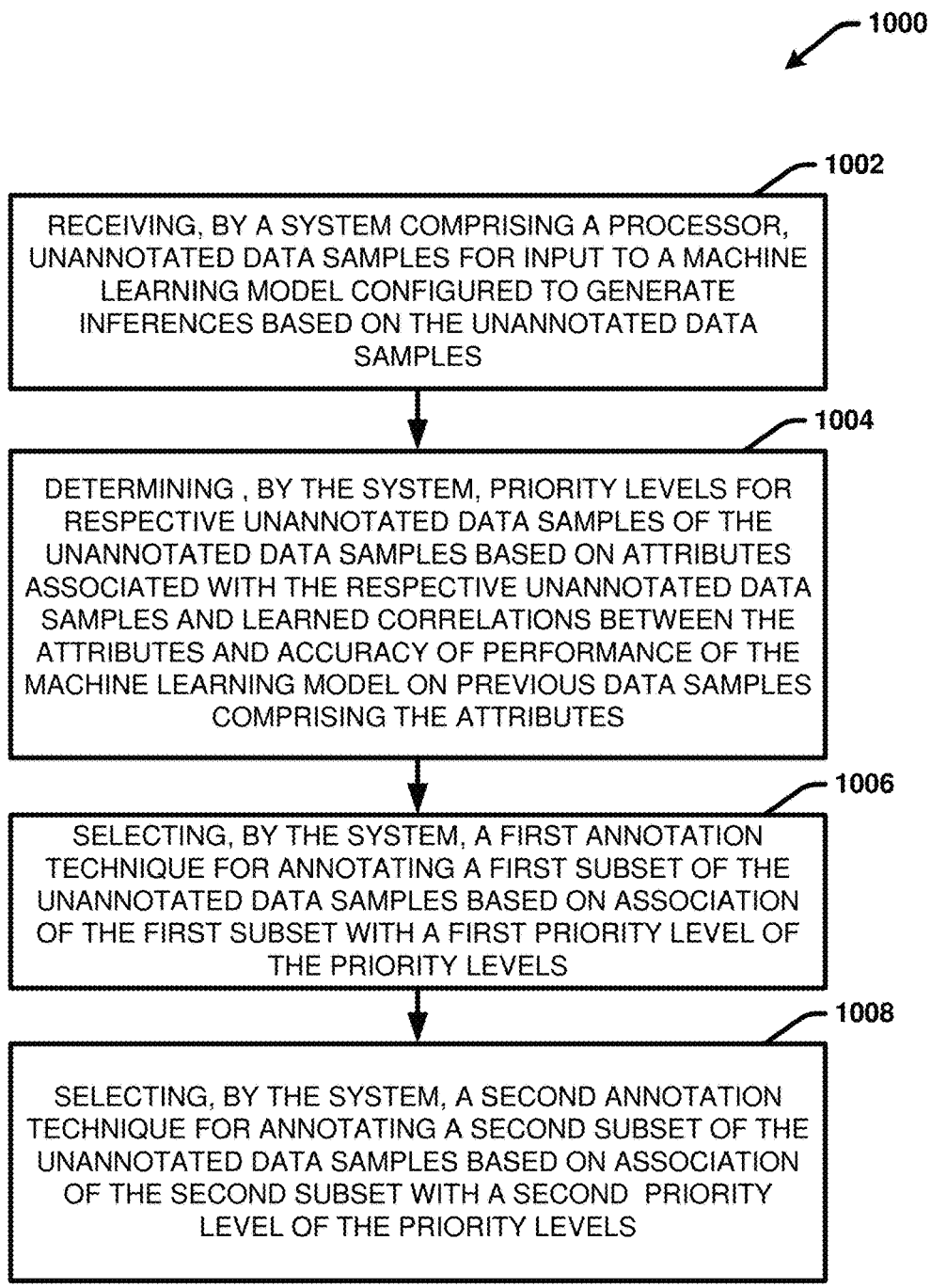
FIG. 10 provides a flow diagram of another example, non-limiting computer-implemented method that facilitates annotating data samples for supervised machine learning algorithms in accordance with one or more embodiments of the disclosed subject matter.

FIG. 10 provides a flow diagram of another example, non-limiting computer-implemented method 1000 that facilitates annotating data samples for supervised machine learning algorithms in accordance with one or more embodiments of the disclosed subject matter. Repetitive description of like elements employed in respective embodiments is omitted for sake of brevity.

At 1002, a system comprising a processor (e.g., system 100, system 200, system 600, system 700, or the like) can receive (e.g., via collection component 202) unannotated data samples (e.g., unannotated data samples 104) for input to a machine learning model configured to generate inferences based on the unannotated data samples (e.g., machine learning model 110, M1). At 1004, the system can determine, (e.g., via the priority evaluation component 206), priority levels for respective unannotated data samples of the unannotated data samples based on attributes associated with the respective unannotated data samples and learned correlations between the attributes and accuracy of performance of the machine learning model on previous data samples comprising the attributes (e.g., using the annotation accuracy and attribute correlation information 212 as determined by the attribute analysis component 702). At 1006, the system can select, a first annotation technique (e.g., a manual annotation technique) for annotating a first subset of the unannotated data samples based on association of the first subset with a first priority level (e.g., a high priority level relative to a defined threshold) of the priority levels (e.g., via annotation management component 204). At 1008, the system can further select, a second annotation technique (e.g., an automated annotation technique) for annotating a second subset of the unannotated data samples based on association of the second subset with a second priority level (e.g., a low priority level relative to a defined threshold) of the priority levels (e.g., via annotation management component 204).

Figure 11:
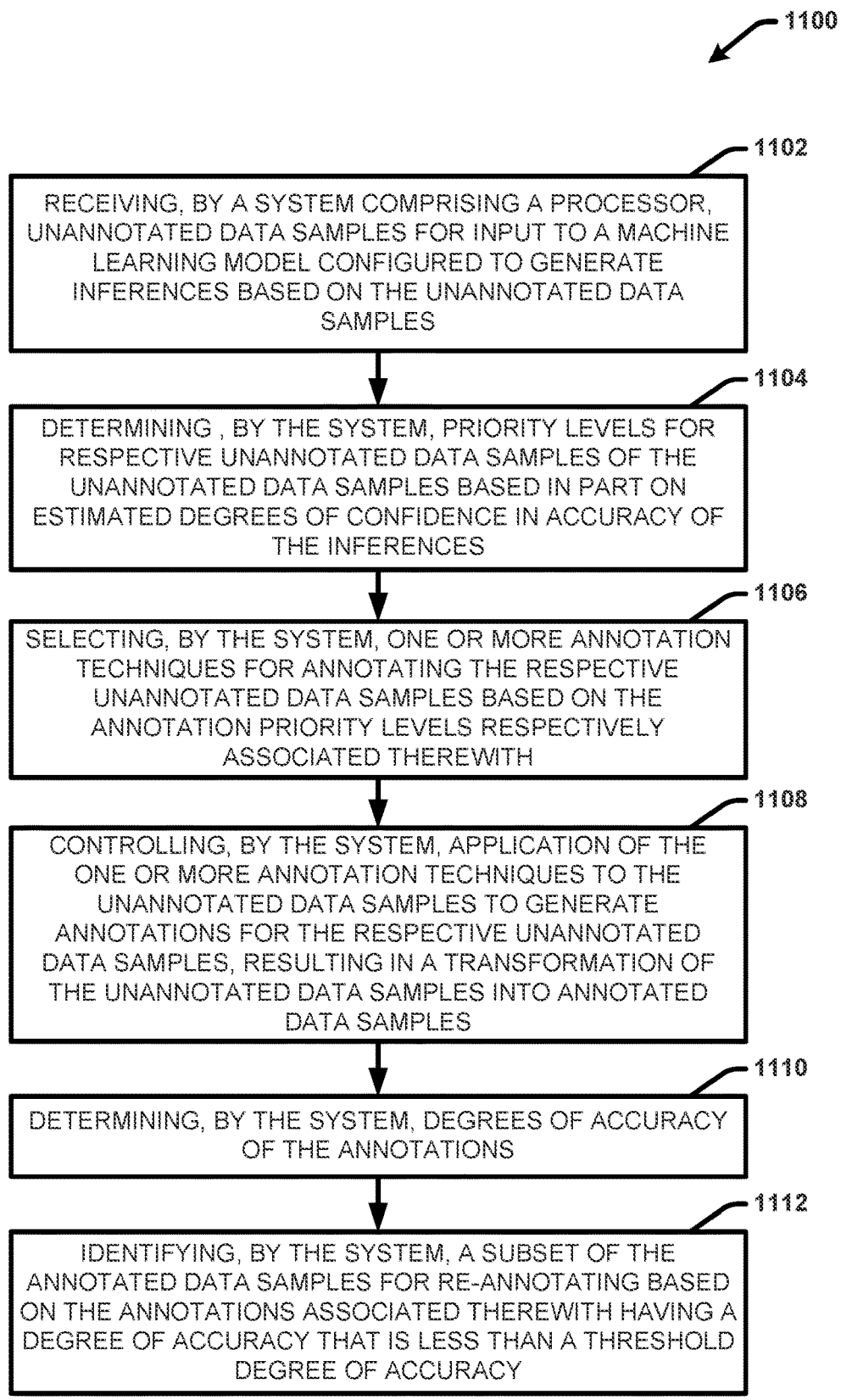
FIG. 11 provides a flow diagram of another example, non-limiting computer-implemented method that facilitates annotating data samples for supervised machine learning algorithms in accordance with one or more embodiments of the disclosed subject matter.

FIG. 11 provides a flow diagram of another example, non-limiting computer-implemented method 1100 that facilitates annotating data samples for supervised machine learning algorithms in accordance with one or more embodiments of the disclosed subject matter. Repetitive description of like elements employed in respective embodiments is omitted for sake of brevity.

At 1102, a system comprising a processor (e.g., system 100, system 200, system 500, system 600, system 700 or the like) can receive (e.g., via collection component 202) unannotated data samples (e.g., unannotated data samples 104) for input to a machine learning model configured to generate inferences based on the unannotated data samples (e.g., machine learning model 110, M1). At 1104, the system can determine priority levels for respective unannotated data samples of the unannotated data samples based in part on the estimated degrees of confidence in accuracy of the inferences (e.g., via priority evaluation component 206). At 1106, the system can select one or more annotation techniques for annotating the respective unannotated data samples based on the annotation priority levels respectively associated therewith. At 1108, the system can control application of the one or more annotation techniques to the unannotated data samples to generate annotations for the respective unannotated data samples (e.g., via annotation component 208), resulting in a transformation of the unannotated data samples into annotated data samples (e.g., annotated data samples 210). At 1110, the system can determine degrees of accuracy of the annotations (e.g., via the annotation accuracy evaluation component 504). At 1012, the system can identify (e.g., via the reprocessing selection component 506)

a subset of the annotated data samples for re-annotating (e.g., the low confidence annotated data samples 518) based on the annotations associated therewith having a degree of accuracy that is less than a threshold degree of accuracy.

Figure 12:
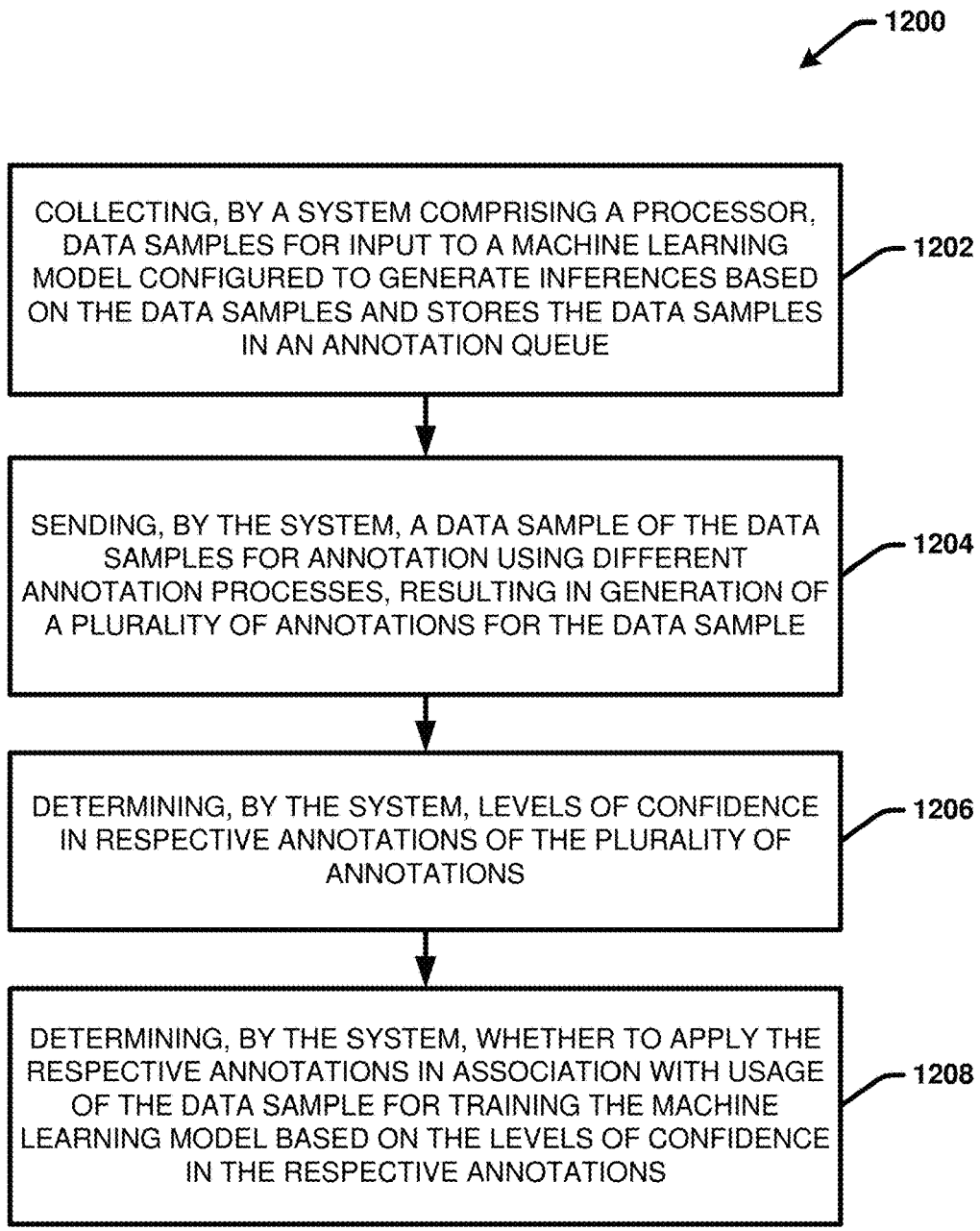
FIG. 12 provides a flow diagram of another example, non-limiting computer-implemented method that facilitates annotating data samples for supervised machine learning algorithms in accordance with one or more embodiments of the disclosed subject matter.

FIG. 12 provides a flow diagram of another example, non-limiting computer-implemented method 1200 that facilitates annotating data samples for supervised machine learning algorithms in accordance with one or more embodiments of the disclosed subject matter. Repetitive description of like elements employed in respective embodiments is omitted for sake of brevity.

At 1202, a system comprising a processor (e.g., system 100, system 200, system 600, system 700, or the like) can collect (e.g., via collection component 202) data samples (e.g., unannotated data samples and/or low confidence annotated data samples 118) for input to a machine learning model configured to generate inferences based on the data samples (e.g., machine learning model 110, M1). At 1204, the system can send (e.g., via annotation management component 204) a data sample of the data samples for annotation using different annotation processes, resulting in generation of a plurality of annotations for the data sample. For example, the annotation management component 204 can send each (or in some implementations one or more) of the collected data samples for annotation using different annotation processes associated with a same annotation technique and/or different annotation processes associated with different annotation techniques. At 1206, the system can determine levels of confidence in respective annotations of the plurality of annotations (e.g., using the annotation accuracy evaluation component 604). At 1208 the system can determine whether to apply the respective annotations in association with usage of the data sample for training the machine learning model based on the levels of confidence in the respective annotations (e.g., using the training selection component 608).

Figure 13:
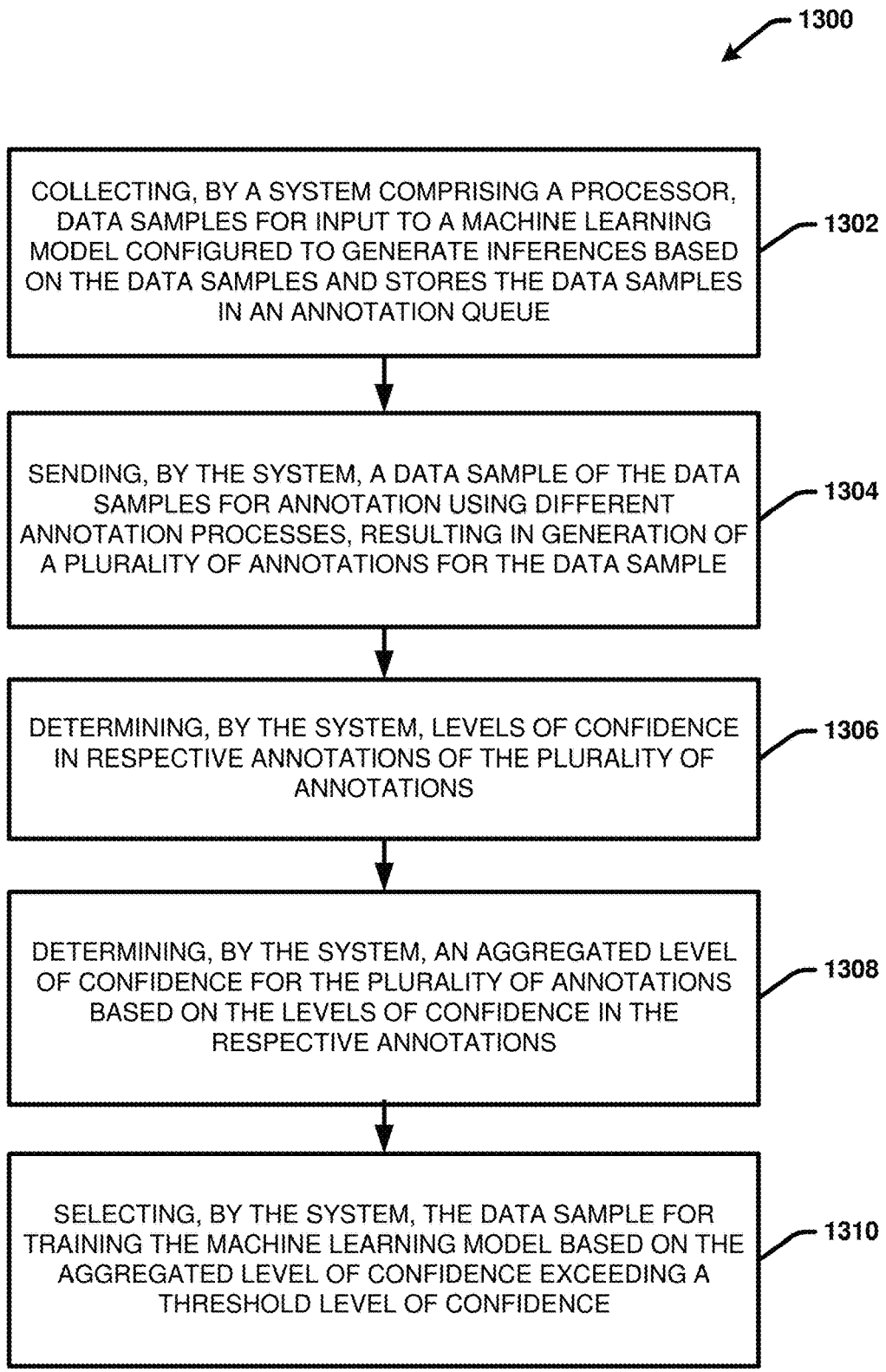
FIG. 13 provides a flow diagram of another example, non-limiting computer-implemented method that facilitates annotating data samples for supervised machine learning algorithms in accordance with one or more embodiments of the disclosed subject matter.

FIG. 13 provides a flow diagram of another example, non-limiting computer-implemented method 1300 that facilitates annotating data samples for supervised machine learning algorithms in accordance with one or more embodiments of the disclosed subject matter. Repetitive description of like elements employed in respective embodiments is omitted for sake of brevity.

At 1302, a system comprising a processor (e.g., system 100, system 200, system 600, system 700, or the like) can collect (e.g., via collection component 202) data samples (e.g., unannotated data samples and/or low confidence annotated data samples 118) for input to a machine learning model configured to generate inferences based on the data samples (e.g., machine learning model 110, M1). At 1304, the system can send (e.g., via annotation management component 204) a data sample of the data samples for annotation using different annotation processes, resulting in generation of a plurality of annotations for the data sample. For example, the annotation management component 204 can send each (or in some implementations one or more) of the collected data samples for annotation using different annotation processes associated with a same annotation technique and/or different annotation processes associated with different annotation techniques. At 1306, the system can determine levels of confidence in respective annotations of the plurality of annotations (e.g., using the annotation accuracy evaluation component 604). At 1308 the system can determine an aggregated level of confidence for the plurality of annotations based on the levels of confidence in the respective annotations (e.g., using the annotation accuracy evaluation component 604). At 1310, the system can select the data sample for training the machine learning model based on the aggregated level of confidence exceeding a threshold level of confidence (e.g., using the training selection component 608).

Figure 14:
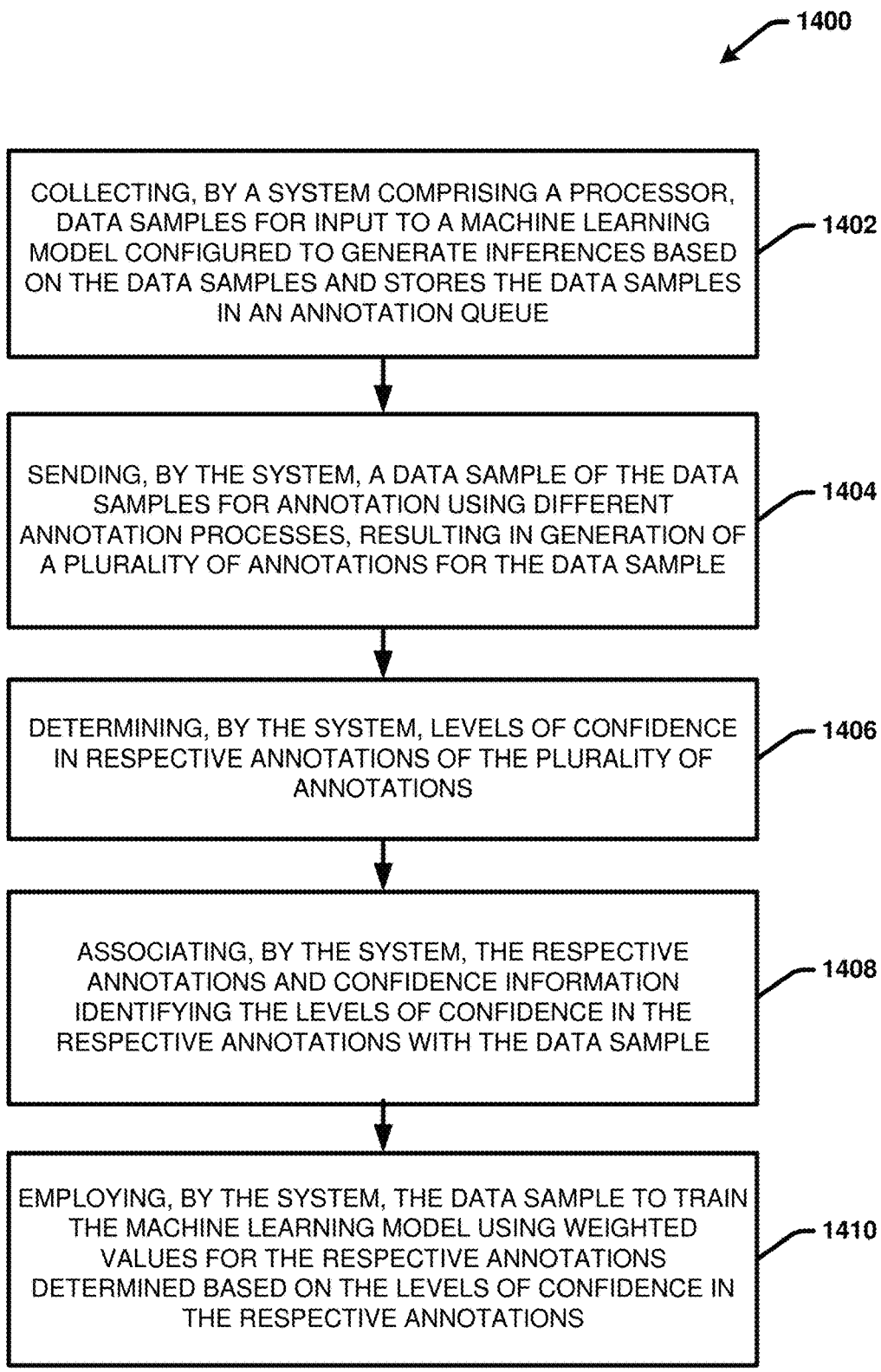
FIG. 14 provides a flow diagram of another example, non-limiting computer-implemented method that facilitates annotating data samples for supervised machine learning algorithms in accordance with one or more embodiments of the disclosed subject matter.

FIG. 14 provides a flow diagram of another example, non-limiting computer-implemented method 1400 that facilitates annotating data samples for supervised machine learning algorithms in accordance with one or more embodiments of the disclosed subject matter. Repetitive description of like elements employed in respective embodiments is omitted for sake of brevity.

At 1402, a system comprising a processor (e.g., system 100, system 200, system 600, system 700, or the like) can collect (e.g., via collection component 202) data samples (e.g., unannotated data samples and/or low confidence annotated data samples 118) for input to a machine learning model configured to generate inferences based on the data samples (e.g., machine learning model 110, M1). At 1404, the system can send (e.g., via annotation management component 204) a data sample of the data samples for annotation using different annotation processes, resulting in generation of a plurality of annotations for the data sample. For example, the annotation management component 204 can send each (or in some implementations one or more) of the collected data samples for annotation using different annotation processes associated with a same annotation technique and/or different annotation processes associated with different annotation techniques. At 1406, the system can determine levels of confidence in respective annotations of the plurality of annotations (e.g., using the annotation accuracy evaluation component 604). At 1408 the system can associate the respective annotations and confidence information identifying the levels of confidence in the respective annotations with the data sample (e.g., using the active learning component 602). At 1410, the system can employ the data sample to train the machine learning model using weighted values for the respective annotations determined based on the levels of confidence in the respective annotations (e.g., using the model development module 108).

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 15, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 15:
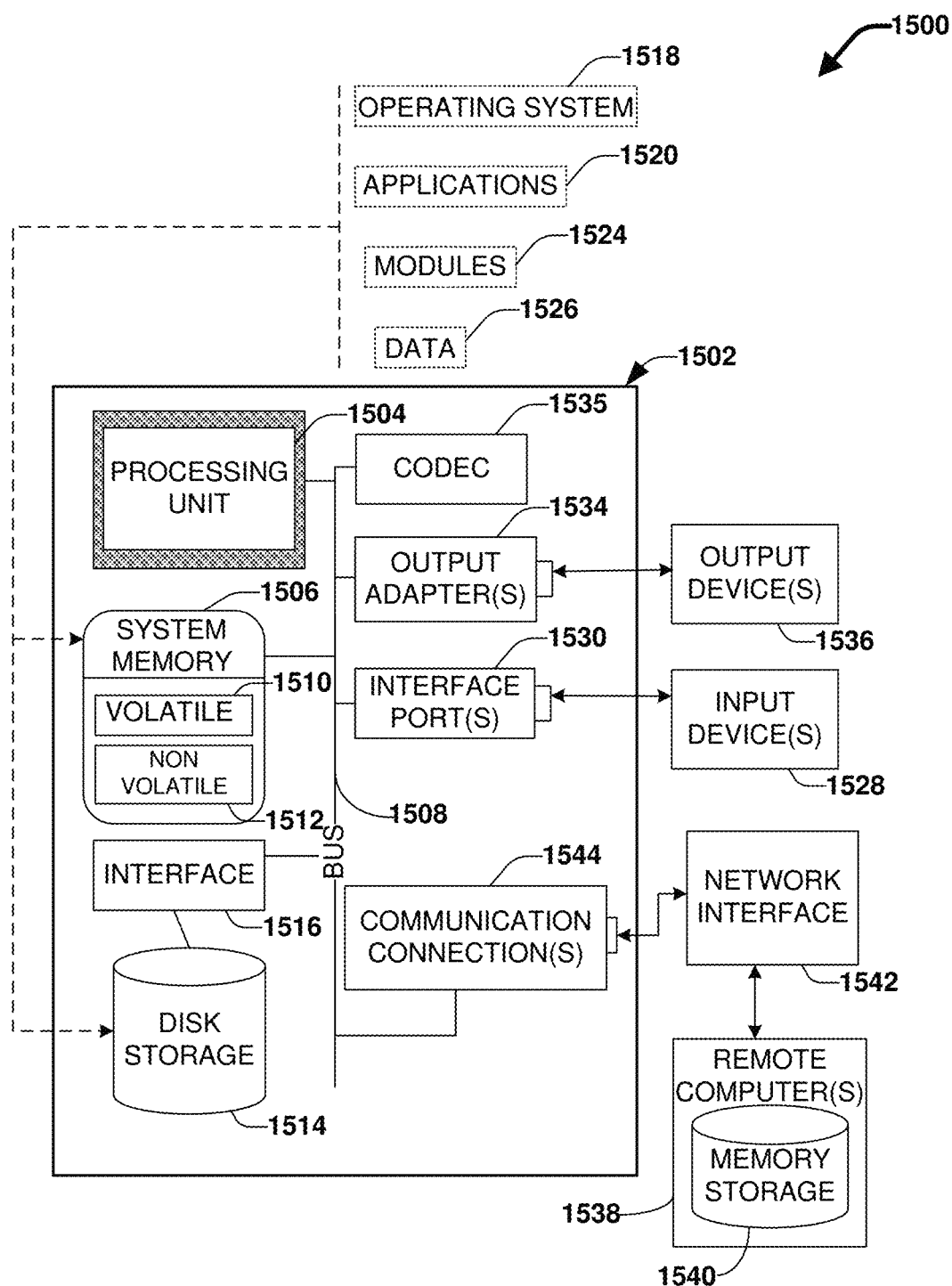
FIG. 15 illustrates a block diagram of an example, non-limiting operating environment in which one or more embodiments described herein can be facilitated.

With reference to FIG. 15, an example environment 1500 for implementing various aspects of the claimed subject matter includes a computer 1502. The computer 1502 includes a processing unit 1504, a system memory 1506, a codec 1535, and a system bus 1508. The system bus 1508 couples system components including, but not limited to, the system memory 1506 to the processing unit 1504. The processing unit 1504 can be any of various available processors. Dual microprocessors and other multiprocessor architectures also can be employed as the processing unit 1504.

The system bus 1508 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1506 includes volatile memory 1510 and non-volatile memory 1512, which can employ one or more of the disclosed memory architectures, in various embodiments. The basic input/output system (BIOS), containing the basic routines to transfer information between elements within the computer 1502, such as during start-up, is stored in non-volatile memory 1512. In addition, according to present innovations, codec 1535 can include at least one of an encoder or decoder, wherein the at least one of an encoder or decoder can consist of hardware, software, or a combination of hardware and software. Although, codec 1535 is depicted as a separate component, codec 1535 can be contained within non-volatile memory 1512. By way of illustration, and not limitation, non-volatile memory 1512 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1512 can employ one or more of the disclosed memory devices, in at least some embodiments. Moreover, non-volatile memory 1512 can be computer memory (e.g., physically integrated with computer 1502 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1510 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1502 can also include removable/non-removable, volatile/non-volatile computer storage medium. FIG. 15 illustrates, for example, disk storage 1514. Disk storage 1514 includes, but is not limited to, devices like a magnetic disk drive, solid state disk (SSD), flash memory card, or memory stick. In addition, disk storage 1514 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1514 to the system bus 1508, a removable or non-removable interface is typically used, such as interface 1516. It is appreciated that disk storage 1514 can store information related to a user. Such information might be stored at or provided to a server or to an application running on a user device. In one embodiment, the user can be notified (e.g., by way of output device(s) 1536) of the types of information that are stored to disk storage 1514 or transmitted to the server or application. The user can be provided the opportunity to opt-in or opt-out of having such information collected or shared with the server or application (e.g., by way of input from input device(s) 1528).

It is to be appreciated that FIG. 15 describes software that acts as an intermediary between users and the basic computer resources described in the suitable operating environment 1500. Such software includes an operating system 1518. Operating system 1518, which can be stored on disk storage 1514, acts to control and allocate resources of the computer 1502. Applications 1520 take advantage of the management of resources by operating system 1518 through program modules 1524, and program data 1526, such as the boot/shutdown transaction table and the like, stored either in system memory 1506 or on disk storage 1514. It is to be appreciated that the claimed subject matter can be implemented with various operating systems or combinations of operating systems.

A user enters commands or information into the computer 1502 through input device(s) 1528. Input devices 1528 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1504 through the system bus 1508 via interface port(s) 1530. Interface port(s) 1530 include, for example, a serial port, a parallel port, a game port, and a universal serial bus (USB). Output device(s) 1536 use some of the same type of ports as input device(s) 1528. Thus, for example, a USB port can be used to provide input to computer 1502, and to output information from computer 1502 to an output device 1536. Output adapter 1534 is provided to illustrate that there are some output devices 1536 like monitors, speakers, and printers, among other output devices 1536, which require special adapters. The output adapters 1534 include, by way of illustration and not limitation, video and sound cards that provide a means of connection between the output device 1536 and the system bus 1508. It should be noted that other devices or systems of devices provide both input and output capabilities such as remote computer(s) 1538.

Computer 1502 can operate in a networked environment using logical connections to one or more remote computers, such as remote computer(s) 1538. The remote computer(s) 1538 can be a personal computer, a server, a router, a network PC, a workstation, a microprocessor based appliance, a peer device, a smart phone, a tablet, or other network node, and typically includes many of the elements described relative to computer 1502. For purposes of brevity, only a memory storage device 1540 is illustrated with remote computer(s) 1538. Remote computer(s) 1538 is logically connected to computer 1502 through a network interface 1542 and then connected via communication connection(s) 1544. Network interface 1542 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1544 refers to the hardware/software employed to connect the network interface 1542 to the bus 1508. While communication connection 1544 is shown for illustrative clarity inside computer 1502, it can also be external to computer 1502. The hardware/software necessary for connection to the network interface 1542 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
    a memory that stores computer executable components; and
    a processor that executes the computer executable components stored in the memory, wherein the computer executable components comprise:
        a collection component that collects unannotated data samples and stores the unannotated data samples in an annotation queue;
        a priority evaluation component that determines annotation priority levels for respective unannotated data samples of the unannotated data samples based on attributes associated with the respective unannotated data samples and correlations between the attributes and accuracy of performance of a machine learning model on previous data samples comprising the attributes;
        an annotation management component that selects, from amongst different annotation techniques, one or more of the different annotation techniques for annotating the respective unannotated data samples based the annotation priority levels associated with the respective unannotated data samples;
        an annotation component that receives annotations applied to the respective unannotated data samples via the one or more different annotation techniques, thereby transforming the unannotated data samples into annotated data samples; and
        a model development module that trains the machine learning model using at least some of the annotated data samples.

2. The system of claim 1, wherein the different annotation techniques are selected from a group consisting of, a manual annotation technique, a supervised learning annotation technique, and a metadata extraction annotation technique.

3. The system of claim 1, wherein the priority evaluation component determines the annotation priority levels based on estimated confidence in the accuracy of inferences that would be generated based on application of the machine learning model to respective unannotated data samples of the unannotated data samples.

4. The system of claim 3, wherein the annotation management component further selects a subset of the unannotated data samples for annotating based on the estimated degrees of confidence associated with the respective unannotated data samples.

5. The system of claim 1, wherein the different annotation techniques comprise a first annotation technique and a second annotation technique, and wherein the annotation component management component selects the first annotation technique for a first subset of the unannotated data samples based on association of the first subset with a first annotation priority level of the annotation priority levels, and selects the second annotation technique for a second subset of the unannotated data samples based on association of the second subset with a second annotation priority level of the annotation priority levels.

6. The system of claim 1, wherein the priority evaluation component further determines the annotation priority levels based on a quantity of annotated training data samples used to train the machine learning model that correspond to the respective unannotated data samples.

7. The system of claim 1, wherein the computer executable components further comprise:
    an active learning component that employs one or more machine learning techniques to learn the correlations.

8. The system of claim 1, wherein the computer executable components further comprise:
    an active learning component that learns one or more attributes of the attributes that are associated with a degree of accuracy of the performance of the machine learning model that is below a threshold degree of accuracy, and wherein the priority evaluation component assigns a high annotation priority level to a subset of the unannotated data samples based on the subset comprising the one or more attributes.

9. The system of claim 1, wherein the computer executable components further comprise:
    an active learning component that learns one or more attributes of the attributes that are associated with a degree of accuracy of the performance of the machine learning model that is above a threshold degree of accuracy, and wherein the priority evaluation component assigns a low annotation priority level to a subset of the unannotated data samples based on the subset comprising the one or more attributes.

10. The system of claim 1, wherein the an annotation component that facilitates applying the one or more different annotation techniques to the unannotated data samples to receive the annotations for the respective unannotated data samples.

11. The system of claim 1, wherein the computer executable components further comprise:
    an annotation accuracy evaluation component that evaluates the annotations and determines levels of confidence in the annotations.

12. The system of claim 11, wherein the annotation accuracy evaluation applies the machine learning model to the respective unannotated data samples to determine the levels of confidence in the annotations.

13. The system of claim 11, wherein the computer executable components further comprise:
    an active learning component that identifies a subset of the annotated data samples for reannotating based on the annotations associated being associated with a level of confidence that is below a threshold level of confidence and sends the subset back to the annotation queue.

14. The system of claim 13, wherein the computer executable components further comprise:
    a feedback component that generates feedback information regarding the subset and facilitates rendering the feedback information at a device associated with an entity responsible for reviewing the subset.

15. The system of claim 11, wherein the active learning component further identifies a subset of the annotated data samples associated with annotations with a confidence level that is above a threshold level of confidence and adds the subset to a set of annotated training data samples for training or updating the machine learning model.

16. The system of claim 15, wherein the model development module employs the set of annotated training data samples to train or update the machine learning model.

17. The system of claim 1, wherein the data samples comprise medical images and wherein the machine learning model is configured to generate medical inferences regarding a medical condition or disease based on the medical images.

18. A method, comprising:
   collecting, by a system comprising a processor, unannotated data samples in an annotation queue;
   determining, by the system, annotation priority levels for respective unannotated data samples of the unannotated data samples based on attributes associated with the respective unannotated data samples and correlations between the attributes and accuracy of performance of a machine learning model on previous data samples comprising the attributes;
   selecting, by the system from amongst different annotation techniques, one or more of the different annotation techniques for annotating the respective unannotated data samples based the annotation priority levels associated with the respective unannotated data samples
   receiving, by the system, annotations applied to the respective unannotated data samples via the one or more different annotation techniques, thereby transforming the unannotated data samples into annotated data samples; and
   training, by the system, the machine learning model using at least some of the annotated data samples.

19. The method of claim 18, wherein the different annotation techniques are selected from a group consisting of, a manual annotation technique, a supervised learning annotation technique, and a metadata extraction annotation technique.

20. The method of claim 18, wherein the determining comprises determining the annotation priority levels based on estimated confidence in the accuracy of inferences that would be generated based on application of the machine learning model to respective unannotated data samples of the unannotated data samples.

21. The method of claim 18, further comprising:
   selecting, by the system, a subset of the unannotated data samples for annotating based on the annotation priority levels associated with the respective unannotated data samples.

22. The method of claim 18, wherein the different annotation techniques comprise a first annotation technique and a second annotation technique, and wherein the selecting further comprises:
   selecting, by the system, the first annotation technique for a first subset of the unannotated data samples based on association of the first subset with a first annotation priority level of the annotation priority levels; and
   selecting, by the system, the second annotation technique for a second subset of the unannotated data samples based on association of the second subset with a second annotation priority level of the annotation priority levels.

23. The method of claim 18, further comprising:
   employing, by the system, one or more active machine learning techniques to learn the correlations.

24. The method of claim 18, further comprising:
   learning, by the system, one or more attributes of the attributes that are associated with a degree of accuracy of the performance of the machine learning model that is below a threshold degree of accuracy; and
   assigning, by the system, a high annotation priority level to a subset of the unannotated data samples based on the subset comprising the one or more attributes.

25. The method of claim 18, further comprising:
   learning, by the system, one or more attributes of the attributes that are associated with a degree of accuracy of the performance of the machine learning model that is above a threshold degree of accuracy; and
   assigning, by the system, a low annotation priority level to a subset of the unannotated data samples based on the subset comprising the one or more attributes.

26. The method of claim 18, further comprising:
   controlling, by the system, application of the one or more different annotation techniques to the unannotated data samples to generate the annotations for the respective unannotated data samples.

27. The method of claim 18, further comprising:
   determining, by the system, levels of confidence in the annotations.

28. The method of claim 27, further comprising:
   identifying, by the system, a subset of the annotated data samples for reannotating based on the annotations associated therewith having a level of confidence that is less than a threshold level of confidence; and
   sending, by the system, by the subset back to the annotation queue based on the identifying.

29. The method of claim 27, further comprising:
   identifying, by the system, a subset of the annotated data samples associated with annotations having a level of confidence that is greater than a threshold level of confidence; and
   employing, by the system, the subset to train or update the machine learning model based on the identifying.

30. A non-transitory machine-readable storage medium, comprising executable instructions that, when executed by a processor, facilitate performance of operations, comprising:
   receiving unannotated data samples;
   determining priority levels for respective unannotated data samples of the unannotated data samples based on attributes associated with the respective unannotated data samples and correlations between the attributes and accuracy of performance of a machine learning model on previous data samples comprising the attributes;
   selecting one or more annotation techniques for annotating the respective unannotated data samples based on the annotation priority levels respectively associated therewith;
   receiving annotations applied to the respective unannotated data samples via the one or more annotation techniques, thereby transforming the unannotated data samples into annotated data samples; and
   training the machine learning model using at least some of the annotated data samples.

31. The non-transitory machine-readable storage medium of claim 30, wherein the operations further comprise:
   employing one or more active machine learning techniques to learn the correlations.

32. The non-transitory machine-readable storage medium of claim 30, wherein the operations further comprise:
- learning one or more attributes of the attributes that are associated with a degree of accuracy of the performance of the machine learning model that is below a threshold degree of accuracy; and
- assigning a high annotation priority level to a subset of the unannotated data samples based on the subset comprising the one or more attributes.

* * * * *